(12) United States Patent
Basude et al.

(10) Patent No.: US 11,883,290 B2
(45) Date of Patent: Jan. 30, 2024

(54) RETRIEVABLE TISSUE GRASPING DEVICES, SPACERS, ARTIFICIAL VALVES AND RELATED METHODS

(71) Applicants: Raghuveer Basude, Fremont, CA (US); Shri Krishna Basude, Fremont, CA (US)

(72) Inventors: Raghuveer Basude, Fremont, CA (US); Shri Krishna Basude, Fremont, CA (US)

(*) Notice: Subject to any disclaimer, the term of this patent is extended or adjusted under 35 U.S.C. 154(b) by 128 days.

(21) Appl. No.: 17/070,783

(22) Filed: Oct. 14, 2020

(65) Prior Publication Data

US 2021/0022850 A1 Jan. 28, 2021

Related U.S. Application Data

(63) Continuation of application No. PCT/US2019/028788, filed on Apr. 23, 2019.

(60) Provisional application No. 62/662,152, filed on Apr. 24, 2018.

(51) Int. Cl.
*A61F 2/24* (2006.01)

(52) U.S. Cl.
CPC ............ *A61F 2/246* (2013.01); *A61F 2/2463* (2013.01); *A61F 2/2466* (2013.01); *A61F 2210/0014* (2013.01); *A61F 2220/0008* (2013.01); *A61F 2250/0003* (2013.01)

(58) Field of Classification Search
CPC ....... A61F 2/246; A61F 2/2463; A61F 2/2466
See application file for complete search history.

(56) References Cited

U.S. PATENT DOCUMENTS

| 9,351,862 | B2 | 5/2016 | Brister et al. |
| 10,779,829 | B2 | 9/2020 | Wei |
| 11,185,413 | B2 | 11/2021 | Basude |
| 11,224,511 | B2 | 1/2022 | Dixon et al. |
| 2004/0220593 | A1 | 11/2004 | Greenhalgh |

(Continued)

FOREIGN PATENT DOCUMENTS

| AU | 2004229028 A1 | 12/2004 |
| CN | 111772874 A | 10/2020 |

(Continued)

OTHER PUBLICATIONS

EP19792190.1 Extended Search Report dated Nov. 15, 2021.
PCT/US2019/028788 International Search Report and Written Opinion of the Searching Authority dated Aug. 22, 2019.

*Primary Examiner* — William H Matthews
(74) *Attorney, Agent, or Firm* — Wilson Sonsini Goodrich & Rosati

(57) ABSTRACT

A clip for immobilizing leaflets of a cardiac or venous valve includes a hub having a pair of tangle resistant spring-biased outer arms coupled to an inferior end of the hub. A pair of tangle-resistant spring-biased inner arms lies adjacent to the outer arms and is coupled to a superior end of the hub. The clip may incorporate adjustable spacers and retrievable post implantation. A delivery catheter is used to position the valve clip adjacent a target valve while the outer and inner arms are biased in an opened position relative to each other. After the valve leaflets are located between the opened outer and inner arms, the biasing forces may be released to allow the clip to self-close over the valve leaflets.

18 Claims, 23 Drawing Sheets

(56) References Cited

U.S. PATENT DOCUMENTS

| | | |
|---|---|---|
| 2011/0066233 A1* | 3/2011 | Thornton ............ A61B 17/068 |
| | | 623/2.37 |
| 2016/0113762 A1* | 4/2016 | Clague ............ A61B 17/00234 |
| | | 623/2.11 |
| 2016/0317290 A1* | 11/2016 | Chau .................... A61F 2/2436 |
| 2018/0008268 A1 | 1/2018 | Khairkhahan |
| 2019/0030285 A1 | 1/2019 | Prabhu et al. |
| 2020/0229806 A1 | 7/2020 | Goldfarb et al. |
| 2020/0383782 A1 | 12/2020 | Basude et al. |
| 2021/0361416 A1 | 11/2021 | Stearns |
| 2022/0023046 A1 | 1/2022 | Basude |
| 2022/0071767 A1 | 3/2022 | Dixon et al. |
| 2022/0117737 A1 | 4/2022 | Abunassar |
| 2022/0296248 A1 | 9/2022 | Abunassar et al. |
| 2022/0346954 A1 | 11/2022 | Abunassar et al. |

FOREIGN PATENT DOCUMENTS

| | | |
|---|---|---|
| CN | 112773563 A | 5/2021 |
| CN | 113288517 A | 8/2021 |
| CN | 113440309 A | 9/2021 |
| CN | 113499169 A | 10/2021 |
| EP | 3484375 A1 | 5/2019 |
| EP | 3484375 A4 | 7/2020 |
| EP | 3740135 A1 | 11/2020 |
| EP | 3740135 A4 | 10/2021 |
| EP | 3923866 A1 | 12/2021 |
| EP | 3923867 A1 | 12/2021 |
| JP | 2002520125 A | 7/2002 |
| JP | 2003511187 A | 3/2003 |
| JP | 2021511123 A | 5/2021 |
| JP | 2022033350 A | 2/2022 |
| JP | 7206191 B2 | 1/2023 |
| WO | WO-2018010370 A1 | 1/2018 |
| WO | WO-2018013856 A1 | 1/2018 |
| WO | WO-2019010370 A1 | 1/2019 |
| WO | WO-2019143726 A1 | 7/2019 |
| WO | WO-2019209871 A1 | 10/2019 |
| WO | WO-2022036209 A1 | 2/2022 |

* cited by examiner

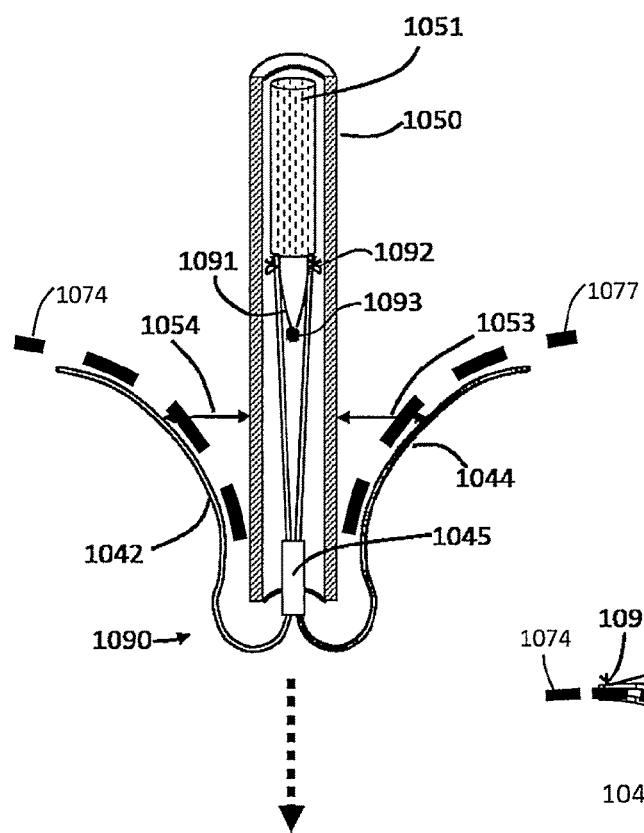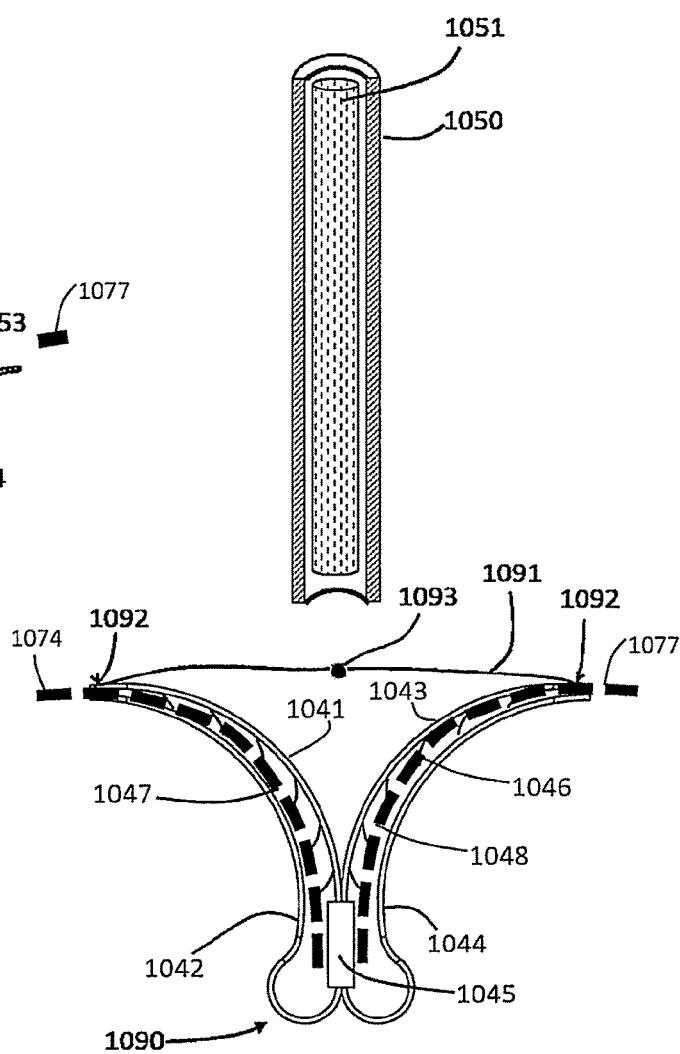

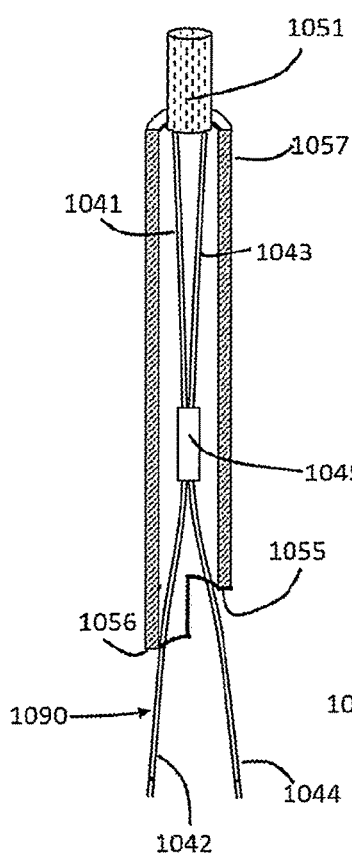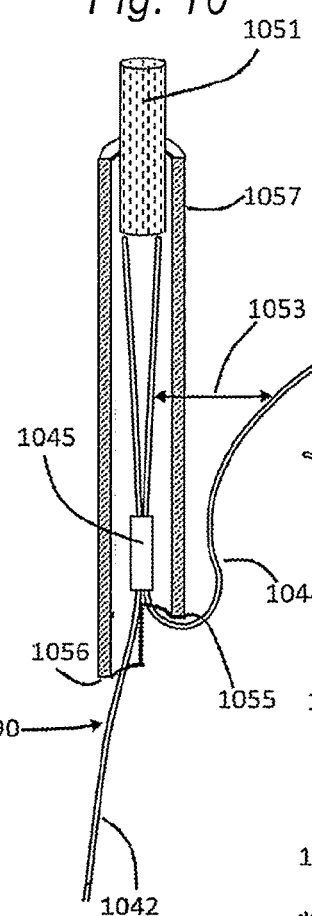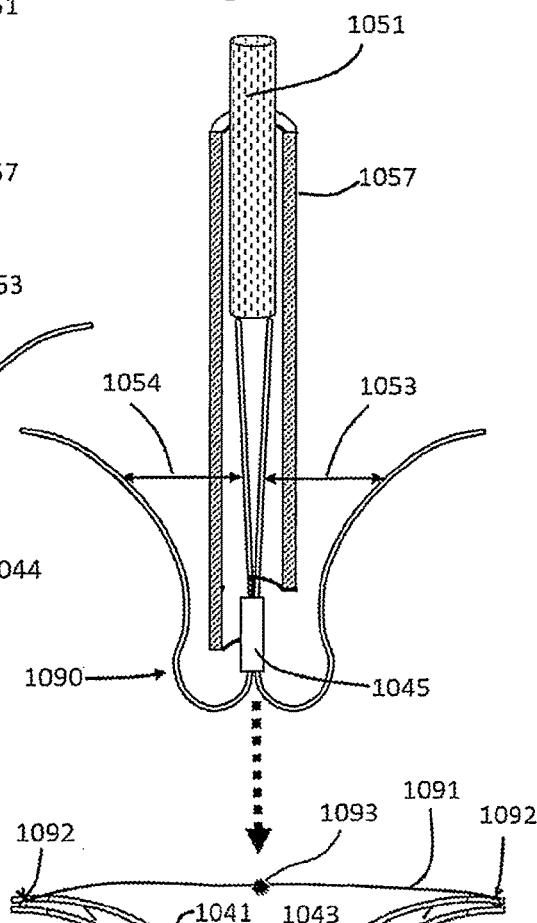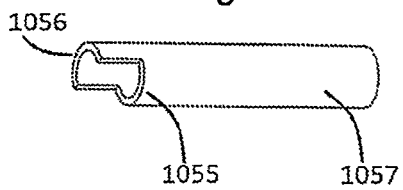

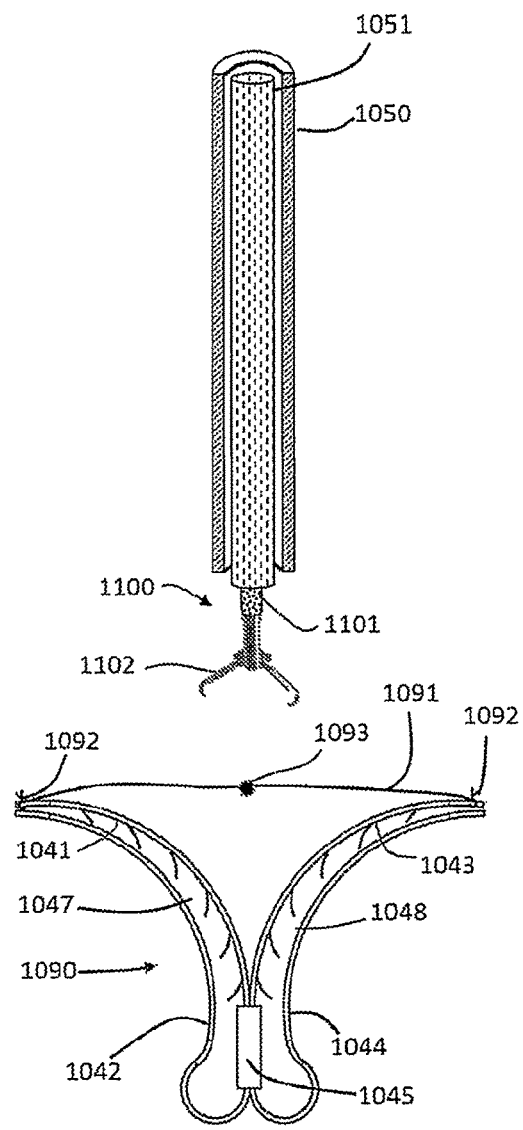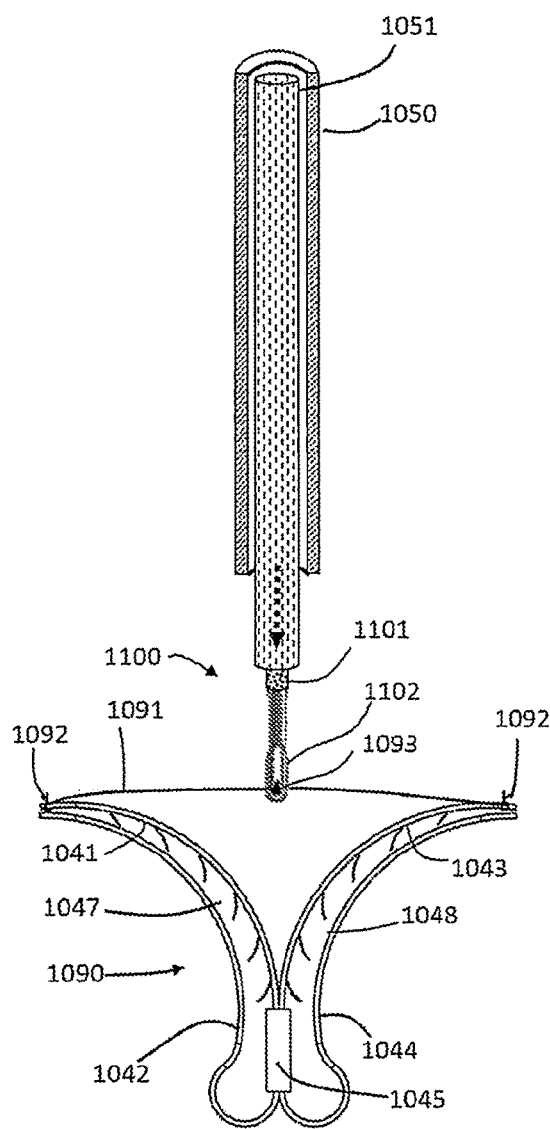

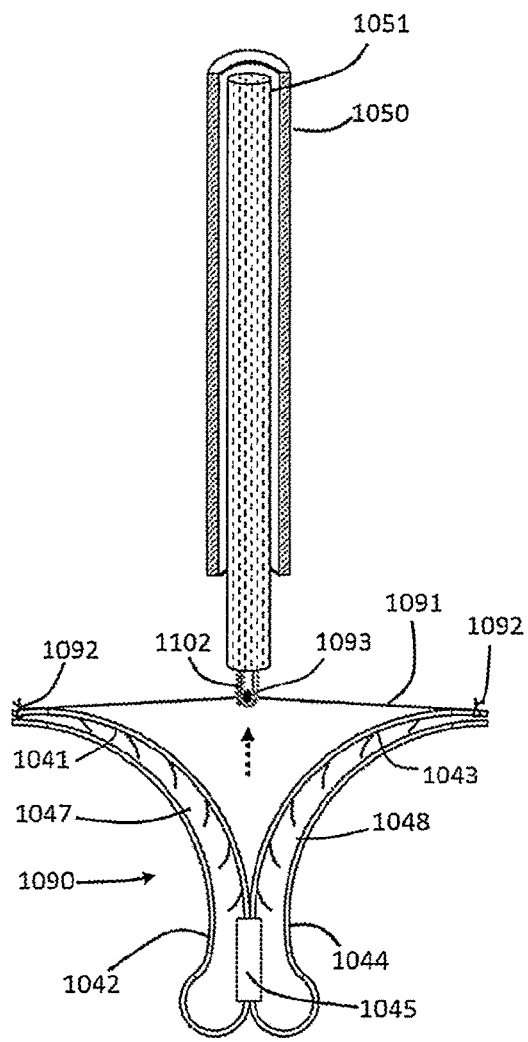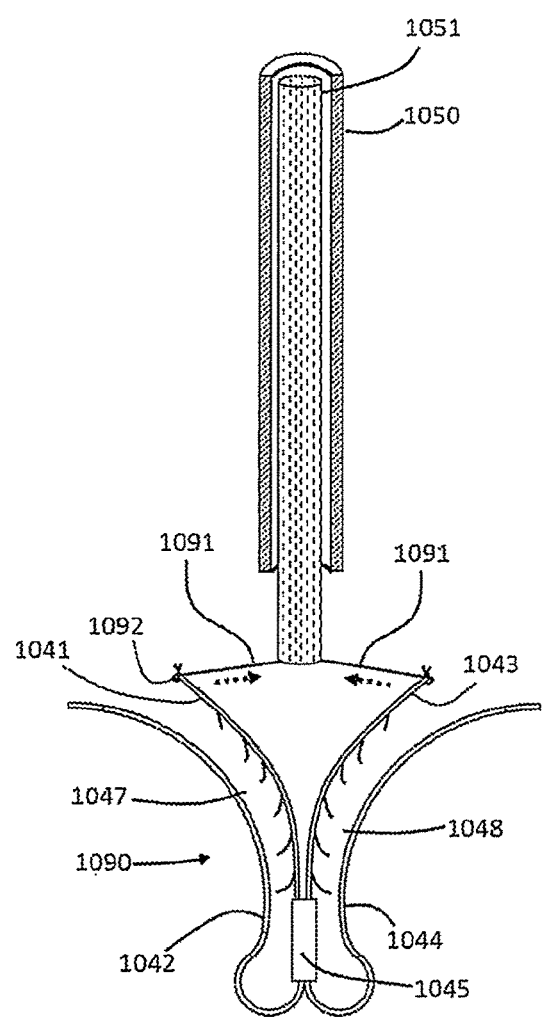

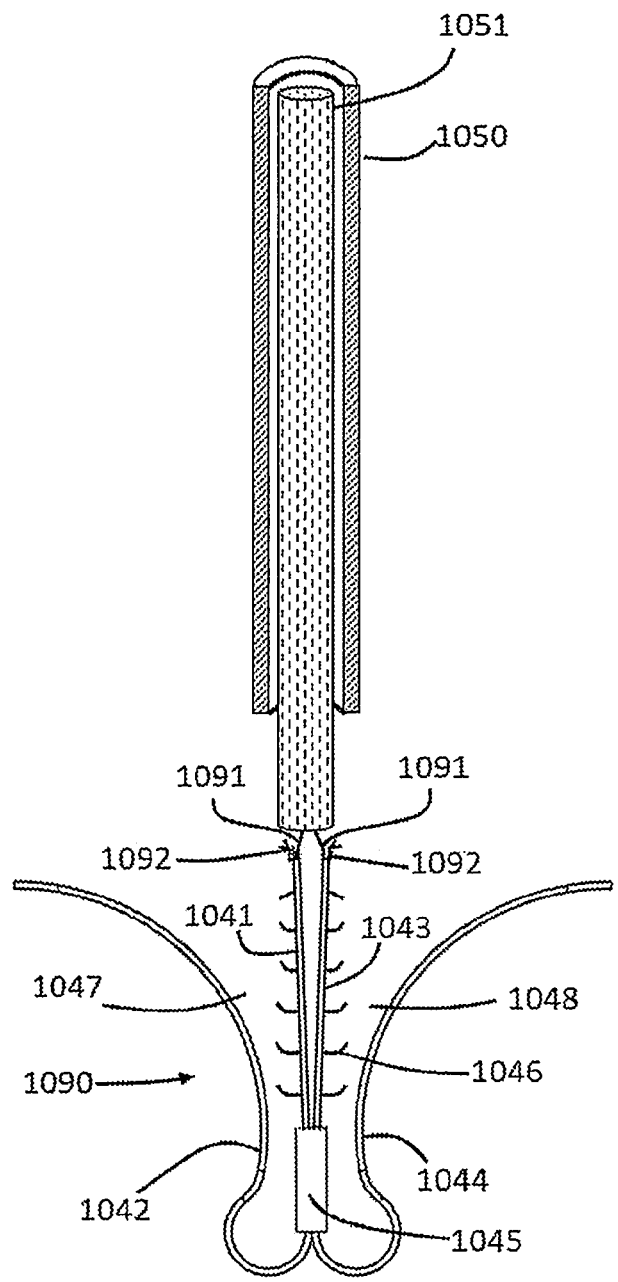

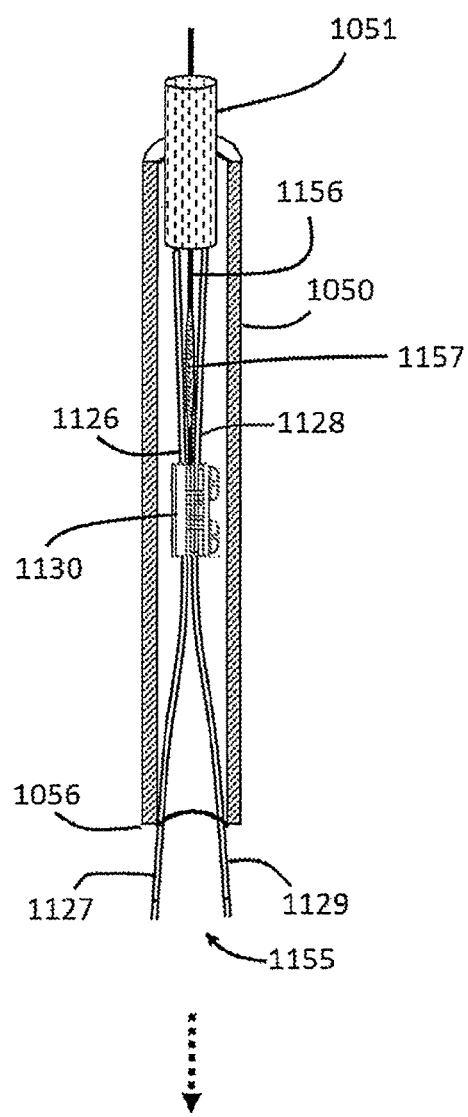
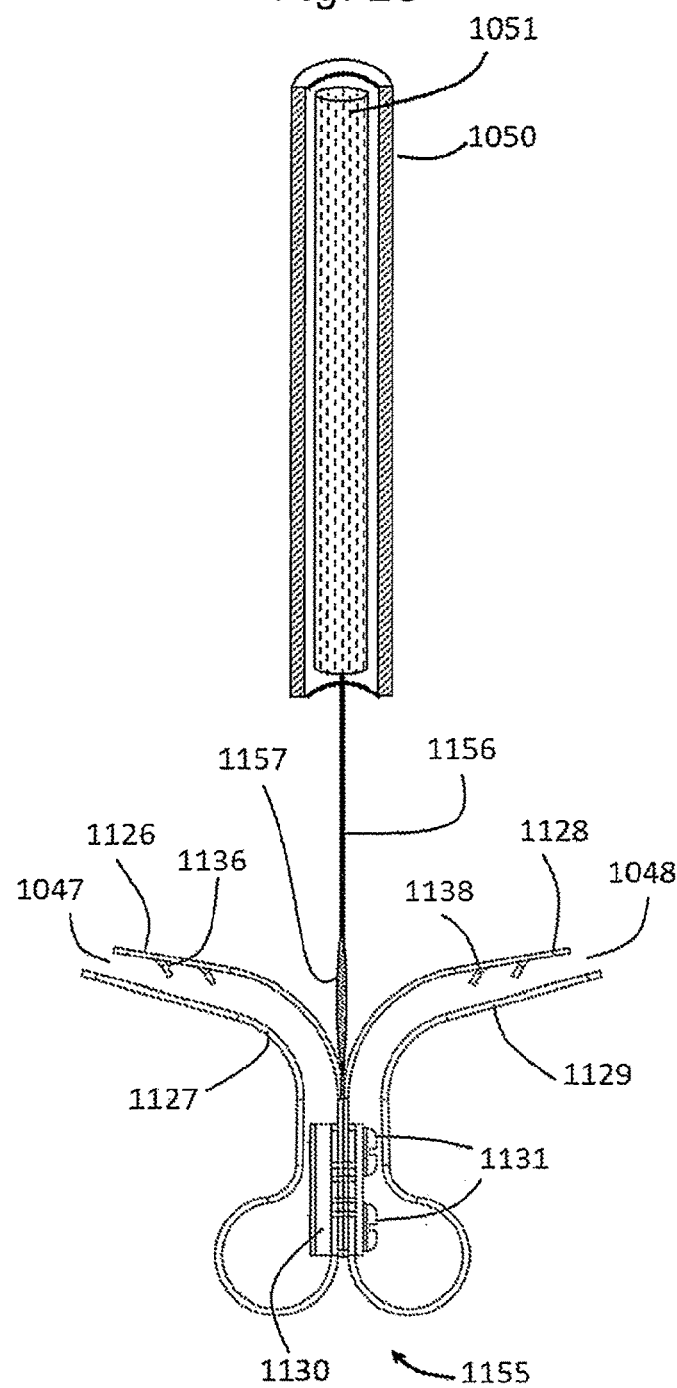
Fig. 27
Fig. 28

RETRIEVABLE TISSUE GRASPING DEVICES, SPACERS, ARTIFICIAL VALVES AND RELATED METHODS

CROSS-REFERENCE TO RELATED APPLICATION

This application is a continuation of PCT Application No. PCT/US2019/028788, filed Apr. 23, 2019, which claims the benefit of U.S. provisional patent application No. 62/662,152, filed on Apr. 24, 2018, the full disclosure of which is incorporated herein by reference.

BACKGROUND OF THE INVENTION

This disclosure pertains generally to medical devices and related methods for helping to seal native heart valves and/or augment and/or replace their function using retrievable tissue grasping devices, spacers, annulus reshaping devices, artificial valves, to prevent or reduce regurgitation there through, as well as delivery devices and related methods for implanting such prosthetic devices. More particularly, the present invention relates to methods and devices for the repair of mitral and tricuspid heart valves, venous valves, and other tissue structure through minimally invasive and other procedures.

The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions or disease. Such damage to the valves can result in serious cardiovascular compromise or death. For many years, the definitive treatment for such disorders was the surgical repair or replacement of the valve during open heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets extending downward from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C" shaped boundary between the abutting free edges of the leaflets when they are closed together When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systole phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Some prior techniques for treating mitral regurgitation include stitching portions of the native mitral valve leaflets directly to one another. The most common treatments for mitral valve regurgitation rely on valve replacement or repair including leaflet and annulus remodeling. The only FDA approved catheter-based device (MitraClip®) available from Abbott) is large (24Fr) owing to complex design and multiple components and equally complex to use/operate. Hence, despite these prior techniques, there is a continuing need for improved devices and methods for treating mitral valve regurgitation.

SUMMARY OF THE INVENTION

This disclosure pertains generally to prosthetic devices and related methods for helping to seal native heart valves and prevent or reduce regurgitation therethrough, as well as devices and related methods for implanting such prosthetic devices.

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, particularly those in which the instruments utilized must negotiate long, narrow, and tortuous pathways to the treatment site. In addition, many of the devices and systems of the invention are adapted to be reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation yet does not require open surgery through the chest and heart wall as in conventional approaches. In addition, the position of the leaflets may vary in diseased mitral valves depending upon the type and degree of disease, such as calcification, prolapse or flail. These types of diseases can result in one leaflet being more mobile than the other (e.g. more difficult to capture), and therefore more difficult to grasp symmetrically in the same grasp with the other leaflet. The features of the present invention allow the fixation devices to be adapted to meet the challenges of unpredictable target tissue geometry, as well as providing a more robust grasp on the tissue once it is captured. Additionally, the invention optionally incorporates visualization techniques to enable the device placement procedure to be performed without the use of general anesthesia.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In an exemplary embodiment, the invention provides a fixation device having a pair of outer arms (or fixation elements), each outer arm having a free end and an engagement surface for engaging the tissue, wherein the outer arms are moveable between a first position for capturing the tissue and a second position for fixing the tissue. Preferably, the engagement surfaces are spaced apart in the first position and are closer together and generally face toward each other in the second position. The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart.

A particular advantage of the present invention is its ability to coapt the leaflets of the mitral valve (or any other tissue with which it is used) in a parallel or vertical relationship as well as grasp the leaflets along its anatomical profile. In other words, even with minimal or no coaptation depth, the leaflets may be captured, drawn together and fixed such that their proximal upstream surfaces are disposed parallel to each other and generally aligned with the direction of flow through the valve at the point of coaptation. In some embodiments of the fixation device, the use of sufficiently rigid outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a close anatomical relationship of the leaflet shape, while grasping alongside the anatomical contours of the leaflets. In other words, the leaflets may be captured, drawn together and fixed such that their natural anatomical shape is retained. In some embodiments of the fixation device, the use of sufficiently flexible outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

The fixation device is preferably delivered with the outer arms in a delivery position configured to minimize the profile of the device. When approaching the mitral valve from the atrial side, some embodiments of the fixation device allow the device to be delivered with the free ends of the outer arms pointing in a generally proximal direction forming an angle of less than about 180°, typically less than 90°, and preferably less than about 40°, relative to the longitudinal axis of the delivery device shaft. In this position the engagement surfaces are facing generally toward each other, being disposed at an angle of less than about 180°, and preferably less than about 40°, relative to each other. For ventricular approaches, in the delivery position the free ends of the outer arms are pointing in a generally distal direction and form an angle of less than about 90°, preferably less than about 40° relative to the longitudinal axis of the delivery device shaft. In this position, the engagement surfaces are facing generally toward each other, usually being disposed at an angle of less than about 180°, and preferably less than about 90°, relative to each other. Alternatively, in some ventricular approaches, it may be preferred to have the free ends of the fixation elements pointing in a generally proximal direction and the engagement surfaces facing away from each other in the delivery position.

In order to provide for the reversibility and removability of the devices and systems of the invention, the leaflets are lifted off the sufficiently flexible arms using sutures or wires. In mitral repair applications, this is particularly important due to the presence of chordae tendineae, valve leaflets and other tissues with which devices may become entangled. For approaches from the atrial side of the mitral valve (in the inverted position), the free ends will be pointing in a generally distal direction relative to the catheter shaft and the engagement surfaces will be facing generally away from each other, usually being disposed at an angle of more than about 180°, and preferably more than 270° relative to each other. For ventricular approaches to the valve in the mimicked inverted position, the free ends will be pointing in a distal direction relative to the catheter shaft and the engagement surfaces will be facing generally toward each other, usually being disposed at an angle of less than about 180°, and preferably less than 90° relative to each other.

In the open position the engagement surfaces of the outer arms preferably form an angle of up to 180° relative to each other so as to maximize the area in which to capture the valve leaflets or other target tissue. The outer arms are preferably flexible to a closed position in which the engagement surfaces engage each other or form an angle as small as 0° relative to each other and or in certain conditions <0° relative to each other, for example −10° relative to each other. The distal arms are configured to be flexible and left permanently in any of various positions while exerting a compressive force opposing the proximal arms to allow for the fixation of tissues of various thickness, geometry, and spacing.

A particular advantage of this invention is that both outer and inner arms are sufficiently superelastic and flexible to exert persistent and gentle opposing forces on the tissue, while allowing for small movements to conform with a) anatomical shape of the leaflet and b) physiological forces on the leaflets.

Another particular advantage of this invention is that the partially atraumatic frictional elements (barbs) are placed medially along the long axis of the arm body and confined by continuous and solid side surface. Unlike in the MitraClip device, the barbs are not exposed along the sides. This is advantageous as it significantly reduces the risk of entanglement of chordae tendineae, valve leaflets and other tissues with which devices may become entangled. Further, this feature reduces the risk of entanglement or sutures or wires or other such delivery catheter elements that may potentially come in contact with the fixation device.

One aspect of the invention provides a tissue shaping device adapted to be deployed in a vessel to reshape tissue adjacent the vessel. In an exemplary embodiment the device comprises of a leaf-spring like apposing features to engage the leaflet from atrial and ventricular sides. Two such leaf-spring features maybe connected at the base to grasp each of the posterior and anterior leaflets of a mitral valve. In some embodiments, the above leaf-springs can be made of sheet metal and/or wire and/or strips and/or any other suitable material form. In some embodiments, the leaf-springs can have anchors and/or barbs to grasp and/or restrain the captured tissue/leaflets.

In some embodiments, the leaf-springs are configured to cinch the annulus in addition to restraining the leaflets to better mitigate regurgitation.

In some embodiments the opposing leaf springs can be formed from a combination of wires and/or sheet metal and/or strips and/or solid and or hollow forms, with or without cut patterns.

In some embodiments, the leaf springs can be expandable and/or compressible, such that they can be in a compressed configuration in the delivery system and be deployed in an expanded configuration.

In some embodiments, the catheter shafts maybe used to manipulate the features of the leaf-springs to capture the leaflets.

In some embodiments, the catheter may use sutures or wires or any other prevalent technique commonly used in the interventional catheter technology to manipulate the leaf-springs to either capture both leaflets at the same time or sequentially capture leaflets.

In some embodiments, only one apposing leaf-spring may used instead of a pair of opposing leaf-springs. This, to capture only one leaflet (anterior or posterior leaflet), while the other leaflet is free.

In some embodiments, a non-captured one of the anterior and posterior mitral valve leaflets is not secured to the sealing device when the prosthetic sealing device is implanted at the native mitral valve.

In some embodiments, advancing a delivery device to a native mitral valve region via a left ventricle comprises inserting the delivery device into the left ventricle through an incision in an apex of the left ventricle.

In some embodiments, advancing the delivery system to the native mitral valve region from the left ventricle comprises inserting the delivery device into the left ventricle through an incision in an apex of the left ventricle.

In some embodiments, when the delivery system is advanced to the native mitral valve region of the heart, the anchor is held in a substantially straightened position within the delivery catheter extending distally along a side of the body of the prosthetic sealing device.

In some embodiments, a method of implanting a prosthetic sealing device at a native mitral valve of a heart comprises of advancing a delivery system to a native mitral valve region of a heart from a left atrium of the heart, the delivery system housing the prosthetic sealing device, proximally retracting an outer sheath of the delivery system such that anchors of the prosthetic sealing device are not confined within the delivery system, retracting the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left atrium comprises advancing the delivery system through an incision in a portion of a septum between the left atrium and a right atrium. In some embodiments, when the delivery system is advanced to the native mitral valve region of the heart, the device is held in a substantially straightened position within the delivery catheter extending proximally from body of the prosthetic sealing device.

In some embodiments, the device is retrievable immediately post deployment. In some embodiments, the device is retrievable in <24 hours post deployment. In some embodiments, the device is retrievable in <30 days post deployment. In some embodiments, the device is retrievable >30 days post deployment. In some embodiments, the device is retrievable in <6 months post deployment. In some embodiments, the device is retrievable >6 months post deployment.

In some embodiments, the device has a spacer feature to mitigate regurgitation. In some embodiments, the spacer feature can be adjusted during the procedure and/or post recovery, and/or at a later date post procedure.

In some embodiments, the device has cinching of leaflet feature to mitigate regurgitation. In some embodiments, the cinching feature can be adjusted during the procedure and/or post recovery, and/or anytime post procedure.

In some embodiments, the device may be configured for veterinary applications to treat valve regurgitation in animals/pets.

Different aspects of the present invention are further described in the following numbered clauses:

Clause 1. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping the leaflet from the ventricular and atrial side, either sequentially (one leaflet at a time) or simultaneously (both leaflets at a time), that is configured to reduce or eliminate or mitigate valve regurgitation, similar to Alfieri edge to edge repair technique.

Clause 2. The method of clause 1, wherein advancing a delivery catheter through the native mitral valve from a left atrium comprises advancing the delivery catheter through an incision in a portion of a septum between the left atrium and a right atrium.

Clause 3. The method of clause 1, wherein advancing a delivery catheter through the native mitral valve from a left ventricle comprises advancing the delivery catheter through an incision in a portion of a septum between the left ventricle and a right ventricle.

Clause 4. The method of clause 1, wherein advancing a delivery catheter through the native mitral valve from a left ventricle comprises advancing the delivery catheter through aortic valve.

Clause 5. The method of clause 1, wherein advancing a delivery device to a native mitral valve region via a left ventricle comprises inserting the delivery device into the left ventricle through an incision in an apex of the left ventricle.

Clause 6. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping a single leaflet from the ventricular and atrial side, wherein the device is configured to prevent the regurgitant flow of blood during systole and during diastole wherein a non-captured one of the anterior and posterior leaflets is not secured to the prosthetic sealing device when the prosthetic sealing device is implanted for intended use at the native mitral valve.

Clause 7. The method of clause 2, wherein advancing a delivery catheter through the native mitral valve from a left atrium comprises advancing the delivery catheter through an incision in a portion of a septum between the left atrium and a right atrium.

Clause 8. The method of clause 2, wherein advancing a delivery catheter through the native mitral valve from a left ventricle comprises advancing the delivery catheter through an incision in a portion of a septum between the left ventricle and a right ventricle.

Clause 9. The method of clause 2, wherein advancing a delivery catheter through the native mitral valve from a left ventricle comprises advancing the delivery catheter through aortic valve.

Clause 10. The method of clause 2, wherein advancing a delivery device to a native mitral valve region via a left ventricle comprises inserting the delivery device into the left ventricle through an incision in an apex of the left ventricle.

Clause 11. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping the leaflet from the ventricular and atrial side, either sequentially (one leaflet at a time) or simultaneously (both leaflets at a time), that is configured to reduce or eliminate or mitigate valve regurgitation, similar to Alfieri edge to edge repair technique; wherein the prosthetic sealing device has a capturable feature that allows for the device to be retrieved.

Clause 12. The method of clause 11, wherein advancing a delivery catheter through the native mitral valve from a left atrium comprises advancing the delivery catheter through an incision in a portion of a septum between the left atrium and a right atrium.

Clause 13. The method of clause 11, wherein advancing a delivery catheter through the native mitral valve from a left ventricle comprises advancing the delivery catheter through an incision in a portion of a septum between the left ventricle and a right ventricle.

Clause 14. The method of clause 11, wherein advancing a delivery catheter through the native mitral valve from a left ventricle comprises advancing the delivery catheter through aortic valve.

Clause 15. The method of clause 11, wherein advancing a delivery device to a native mitral valve region via a left ventricle comprises inserting the delivery device into the left ventricle through an incision in an apex of the left ventricle.

Clause 16. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping a single leaflet from the ventricular and atrial side, wherein the device is configured to prevent the regurgitant flow of blood during systole and during diastole wherein a non-captured one of the anterior and posterior leaflets is not secured to the prosthetic sealing device when the prosthetic sealing device is implanted for intended use at the native mitral valve; wherein the prosthetic sealing device has a capturable feature that allows for the device to be retrieved.

Clause 17. The method of clause 16, wherein advancing a delivery catheter through the native mitral valve from a left atrium comprises advancing the delivery catheter through an incision in a portion of a septum between the left atrium and a right atrium.

Clause 18. The method of clause 16, wherein advancing a delivery catheter through the native mitral valve from a left ventricle comprises advancing the delivery catheter through an incision in a portion of a septum between the left ventricle and a right ventricle.

Clause 19. The method of clause 16, wherein advancing a delivery catheter through the native mitral valve from a left ventricle comprises advancing the delivery catheter through aortic valve.

Clause 20. The method of clause 16, wherein advancing a delivery device to a native mitral valve region via a left ventricle comprises inserting the delivery device into the left ventricle through an incision in an apex of the left ventricle.

Clause 21. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping the leaflet from the ventricular and atrial side, either sequentially (one leaflet at a time) or simultaneously (both leaflets at a time), and has a spacer feature that is configured to reduce or eliminate or mitigate valve regurgitation.

Clause 22. The method of clause 21, wherein advancing a delivery catheter through the native mitral valve from a left atrium comprises advancing the delivery catheter through an incision in a portion of a septum between the left atrium and a right atrium.

Clause 23. The method of clause 21, wherein advancing a delivery catheter through the native mitral valve from a left ventricle comprises advancing the delivery catheter through an incision in a portion of a septum between the left ventricle and a right ventricle.

Clause 24. The method of clause 21, wherein advancing a delivery catheter through the native mitral valve from a left ventricle comprises advancing the delivery catheter through aortic valve.

Clause 25. The method of clause 21, wherein advancing a delivery device to a native mitral valve region via a left ventricle comprises inserting the delivery device into the left ventricle through an incision in an apex of the left ventricle.

Clause 26. The method of clause 21, wherein the spacer is expandable.

Clause 27. The method of clause 21, wherein the spacer is collapsible.

Clause 28. The method of clause 21, wherein the spacer is compressible.

Clause 29. The method of clause 21, wherein the spacer is inflatable.

Clause 30. The method of clause 21, wherein the spacer is solid.

Clause 31. The method of clause 21, wherein the spacer is hollow.

Clause 32. The method of clause 21, wherein the spacer is porous.

Clause 33. The method of clause 21, wherein the spacer is non-porous.

Clause 34. The method of clause 21, wherein the spacer is incompressible.

Clause 35. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and or straightened configuration; advancing the prosthetic sealing device distally relative to the delivery catheter such that prosthetic sealing device moves out of the catheter and forms a leaflet-engaging structure capable of capturing or grasping a single leaflet from the ventricular and atrial side, wherein the device is configured to prevent the regurgitant flow of blood during systole and during diastole wherein a non-captured one of the anterior and posterior leaflets is not secured to the prosthetic sealing device when the prosthetic sealing device is implanted for intended use at the native mitral valve; and has a spacer feature that is configured to reduce or eliminate or mitigate valve regurgitation.

Clause 36. The method of clause 35, wherein advancing a delivery catheter through the native mitral valve from a left atrium comprises advancing the delivery catheter through an incision in a portion of a septum between the left atrium and a right atrium.

Clause 37. The method of clause 35, wherein advancing a delivery catheter through the native mitral valve from a left ventricle comprises advancing the delivery catheter through an incision in a portion of a septum between the left ventricle and a right ventricle.

Clause 38. The method of clause 35, wherein advancing a delivery catheter through the native mitral valve from a left ventricle comprises advancing the delivery catheter through aortic valve.

Clause 39. The method of clause 35, wherein advancing a delivery device to a native mitral valve region via a left ventricle comprises inserting the delivery device into the left ventricle through an incision in an apex of the left ventricle.

Clause 40. The method of clause 35, wherein the spacer is expandable.

Clause 41. The method of clause 35, wherein the spacer is collapsible.

Clause 42. The method of clause 35, wherein the spacer is compressible.

Clause 43. The method of clause 35, wherein the spacer is inflatable.

Clause 44. The method of clause 35, wherein the spacer is solid.

Clause 45. The method of clause 35, wherein the spacer is hollow.

Clause 46. The method of clause 35, wherein the spacer is porous.

Clause 47. The method of clause 35, wherein the spacer is non-porous.

Clause 48. The method of clause 35, wherein the spacer is incompressible.

Clause 49. The method of any of the above clauses, comprising a capture feature that allows for retrieval of device during and/or post deployment.

Clause 50. The method of Clause 49, wherein the capture feature can be used to actuate at least one component of the prosthetic sealing device during and/or post implantation.

Clause 51. The method of any of the above clauses, wherein, the prosthetic device can be retrieved post implantation within 1 day, 1 week, 1 month, 1 year, 10 years, 20 years, 30 years, 50 years, 100 years and/or 120 years.

Clause 52. The method of any of the above clauses, wherein, the prosthetic device can be retrieved post implantation after 0 days, 1 day, 1 week, 1 month, 1 year, 10 years, 20 years, 30 years, 50 years, 100 years and/or 120 years.

Clause 53. The method of any of the above clauses, comprising a sensor, transducer, actuator and/or one or more imaging features to aid, adjust, implant, retrieve and/or monitor the functionality, safety and/or efficacy of the prosthetic device.

Clause 54. The method of any of the above clauses, comprising of any combination claims, clauses or embodiments described in this invention.

BRIEF DESCRIPTION OF THE DRAWINGS

FIG. 7 shows the device pushed out in an exemplary leaflet grasping configuration. The leaflets can be grasped in the gaps 1053, 1054.

FIG. 8 shows the exemplary embodiment of the device 1090 post deployment. For simplicity, the leaflets are not shown within the gaps 1047 and 1048. It additionally shows the retrieval suture 1091 with radio-opaque marker 1093.

FIGS. 9-13 show a method of deploying the exemplary device embodiment of 1090 from a stepped delivery sheath that allows for sequential engagement of leaflets.

FIGS. 15-22 show a method of retrieving the exemplary device embodiment 1090 post implantation.

FIGS. 27-30 show deployment steps of an exemplary embodiment of the implant device 1155.

FIG. 32 shows the schematic of the exemplary embodiment 1150 implanted in the mitral valve during systole, while

FIG. 34 shows the schematic of the exemplary embodiment 1155 implanted in the mitral valve during systole, while

DETAILED DESCRIPTION OF THE INVENTION

Figure 1:
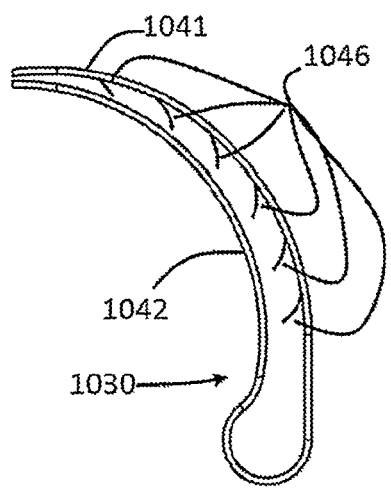
FIG. 1 shows an exemplary embodiment of a device configured to capture any one of the anterior or posterior leaflets.

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another. Further, although the primary intention is for use in humans, the disclosed embodiments may be configured to be used in animals too.

Grasping will preferably be atraumatic, which provides a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

The devices and methods of the invention rely upon the use of a minimally invasive and/or an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve and tricuspid valve.

The prosthetic device can be configured to be implanted via a delivery sheath. The body and the anchor can be a solid or hollow, compressible or incompressible and rigid or flexible. The device can be configured to allow the anchor to self-expand radially or laterally away from the body initially in order to create a gap between the body and the anchor. The leaflet can then be positioned in the gap. The body can then be allowed to contact the leaflet, closing the gap between the body and the anchor and capturing the leaflet between the body and the anchor. The implantation methods for various embodiments can be different, and are more fully discussed below with respect to each embodiment.

Some embodiments disclosed herein are generally configured to be secured to only one of the native mitral leaflets. However, other embodiments comprise more than one anchor and can be configured to be secured to both mitral leaflets. Further, there are other embodiments with anchors that allow for retrieval of the implanted body at a later date.

Unless otherwise stated, any of the embodiments disclosed herein that comprise a single anchor can optionally be secured to the anterior mitral leaflet or secured to the posterior mitral leaflet or secured to both regardless of whether the particular embodiments are shown as being secured to a particular one of the leaflets.

Some embodiments disclosed herein are generally configured with an anchor or anchor-like support structures that have coatings or coverings to promote tissue incorporation over chronic conditions. However, other embodiments comprise of biocompatible coatings or coverings that promote minimal or no tissue ingrowth—so as to enable device retrieval/removal at a later date. Unless otherwise stated, any of the embodiments may be configured to a) fully incorporate tissue, b) partially incorporate tissue, or c) minimal to no incorporation of tissue or a combination of tissue incorporation at various sites of the device, regardless of whether the particular embodiments are shown as being covered or coated.

Some embodiments disclosed herein include a spacer feature that can be used to fill the regurgitant orifice, to further mitigate and/or eliminate valve regurgitation. Unless otherwise stated, any of the embodiments disclosed herein can optionally include spacers, regardless of whether the particular embodiments are shown with a spacer or not.

Furthermore, some embodiments can optionally also include one or more atrial and or ventricle anchors, such as to provide additional stabilization. Unless otherwise stated, any of the embodiments disclosed herein can optionally include an atrial (and or ventricle) anchor or not include an atrial (and or ventricle) anchor, regardless of whether the particular embodiments are shown with an atrial (and or ventricle) anchor or not.

Figure 2:
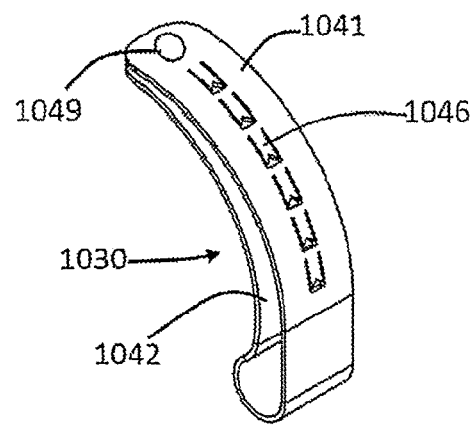
FIG. 2 shows a perspective view of the exemplary embodiment shown in FIG. 3.

FIGS. 1 and 2 shows an exemplary embodiment of a prosthetic device 1030 that comprises of a atrial leaf-spring 1041 and ventricular leaf-spring 1042 that are contiguous. Either atrial and/or ventricular leaf-springs 1041, 1042 can have anchors or barbs or frictional elements (exemplary atrial frictional elements 1046 are shown in FIGS. 1 and 2. These anchors can be configured to be atraumatic and designed to release or restrain the tissue depending on the gap between the two leaf-springs 1041, 1042. The gap between the leaf-springs 1041 and 1042 can be manipulated using prevalent intervention catheter technology such as pulling the atrial leaf-spring 1041 using a sutures or wires while restraining the ventricular leaf-spring 1042 using catheter shaft and/or sutures/wires and/or custom delivery mechanisms. FIG. 2 shows a perspective view of the exemplary embodiment shown in FIG. 1, further illustrating a hole feature 1049 at the top of atrial leaf-spring 1041 which can be used for attaching a retrieval suture loop 1091 as described below.

Figure 3:
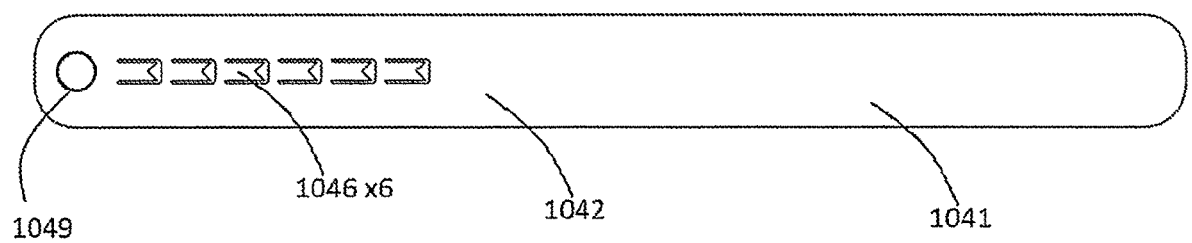
FIG. 3. Shows the (sheet metal) laser-cut flat pattern of the exemplary embodiment shown in FIG. 1.

FIG. 3 shows the prosthetic device 1030 in a straightened form prior for bending the final spring form. A blank or strip may be cut into the pattern illustrated in FIG. 3, typically being laser-cut from a sheet of superelastic nickel-titanium or other alloy (such as Nitinol®). In other embodiments, the device 1030 can be made of elastic polymers, metals, ceramics of the combinations of thereof.

Figure 4:
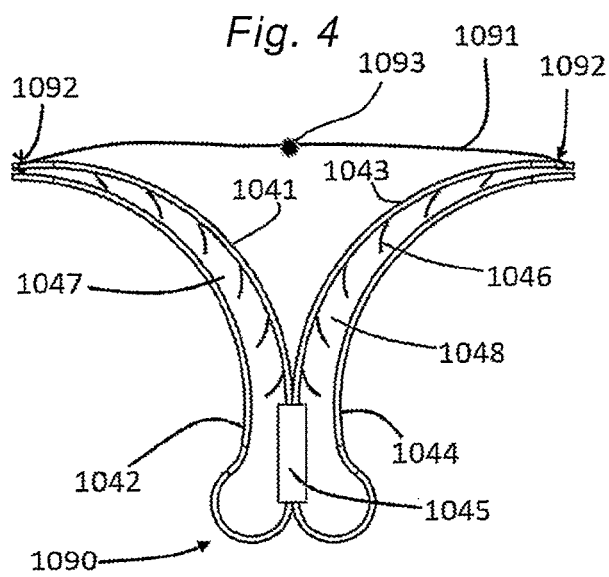
FIG. 4 shows an exemplary embodiment of a device that is formed by combining two of the exemplary embodiments shown in FIG. 1. This, to capture each of the anterior and posterior mitral valve leaflets.

FIG. 4 shows an exemplary embodiment of device 1090, which is formed using two devices 1030 (as shown previously in FIG. 1), which are fastened/bonded/welded/crimped together at the base, in this case using a tubular or rectangular fastening member 1045 that lashes or otherwise secures the two devices 1030 together in a face-to-face manner. By securing the devices 1030 near their respective bases, the atrial leaf springs 1041 are free to bend in order to capture and/or release leaflets. Additionally, the embodiment may include a retrieval suture loop 1091 with a radio-opaque marker 1093.

Figure 5:
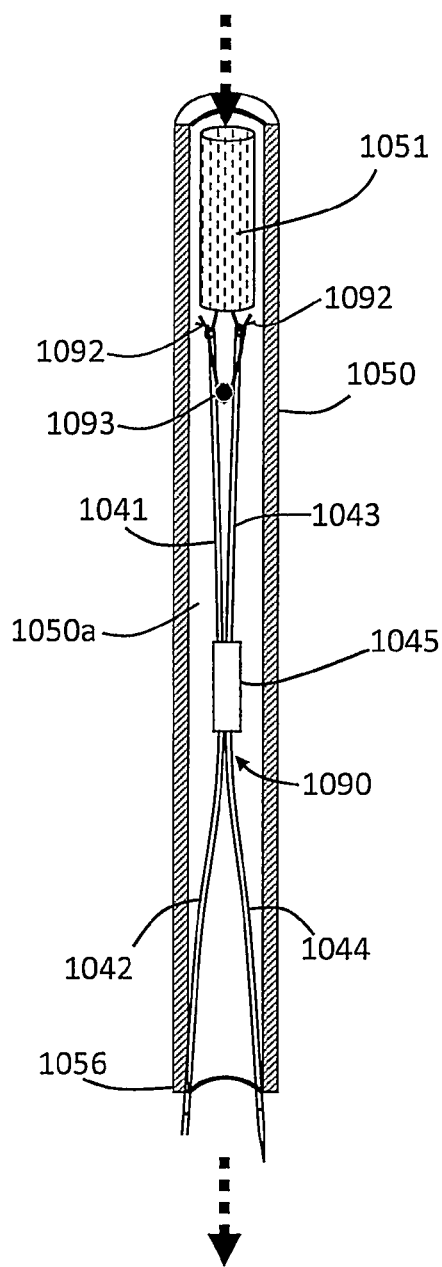
FIG. 5 shows an exemplary embodiment of a device 1090 in a straightened configuration inside a delivery catheter 1050 having a delivery lumen 1050*a* with individual capture springs of the device are in a constrained, straightened configuration.

FIGS. 5-8 illustrate an exemplary method of deployment of the device 1090 from a delivery catheter 1050. In FIG. 5, the device 1090 is shown mostly within the catheter 1050 with the atrial leaf-springs 1041, 1043 extending proximally while ventricular leaf-springs 1042, 1044 are extended distally, in a straightened, or unfurled, state. A pusher member 1051 can be used to push the device 1090 distally relative to the catheter 1050 or to hold the device 1090 steady as the catheter is retracted. The device 1090 will typically be detachably attached to the pusher member 1051 by the retrieval suture loop 1091 and suture loops 1092.

Figure 6:
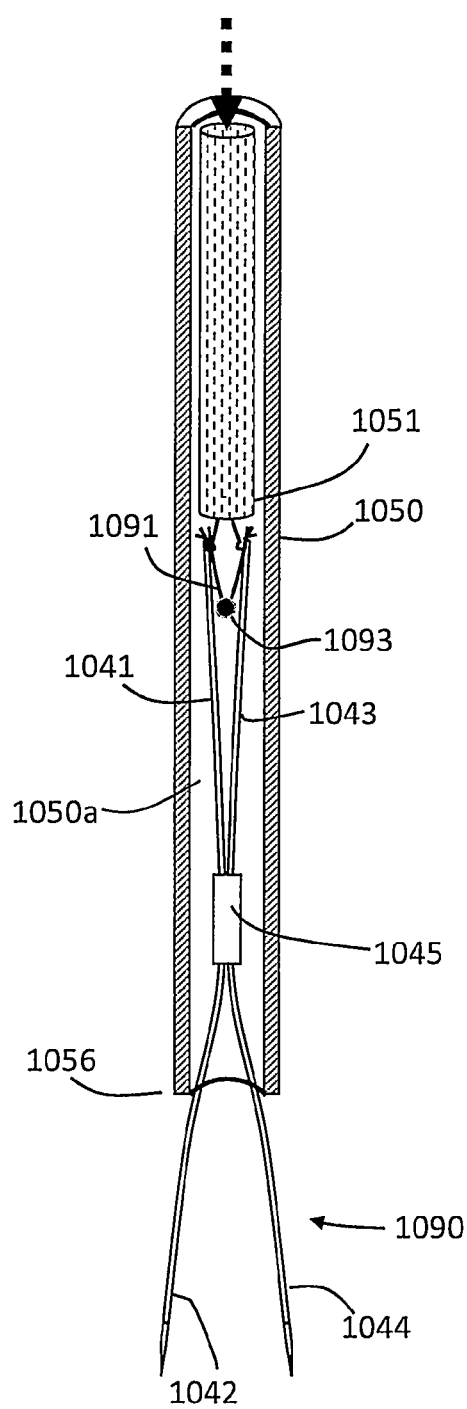
FIG. 6 shows the exemplary embodiment the device 1090 being deployed pushing the device distally relative to the delivery catheter 1050 or vice-versa by retracting the delivery catheter proximally relative to the delivery catheter

In FIG. 6, the device 1090 is deployed by pushing distally relative to the catheter 1050 such that the ventricular leaf-springs 1042, 1044 begin to extend out of a distal end 1056 of the catheter 1050. As shown in FIG. 7, the ventricular leaf-springs 1042, 1044 fully emerge from the distal end 1056 and elastically return to their predetermined shapes.

The mitral leaflet 1074, 1077 may be initially captured within large gaps 1053, 1054 between the inner surfaces of the ventricular leaf-springs 1042, 1044 and an outer surface of a distal region of the delivery catheter 1050 which form after the ventricular leaf-springs emerge from the delivery catheter, as shown in FIG. 7. After the entire device 1090 has emerged from the catheter 1050, as shown in FIG. 8, the atrial leaf springs 1041, 1042 close over the atrial surfaces of the mitral valve leaflets 1074, 1077 as the atrial leaf springs return to their unconstrained shapes. In this way, the leaflets 1074, 1077 are captured/anchored within the smaller gaps 1047, 1048.

As shown in FIG. 8, the device 1090 fully separates from the delivery catheter 1050, and the ventricular leaf springs 1042, 1044 elastically return to their pre-deformation shape once the device is fully released from constraint of the delivery catheter 1050.

FIGS. 9-11 illustrate an exemplary method of deployment of the device 1090 from a delivery catheter 1057, wherein, the user can sequentially grab and or constrain one leaflet at a time. This method is slightly modified method as illustrated and described earlier in FIGS. 5-8, wherein, all components except the distal end of the catheter shaft 1057 is stepped that is, there is a leading distal edge 1056 and a trailing edge 1055 as shown in FIG. 12. In FIG. 9, the device 1090 is shown mostly within the catheter 1057 with the atrial leaf-springs 1041, 1043 extending proximally while ventricular leaf-springs 1042, 1044 are extended distally, in a straightened, or unfurled, state. A pusher member 1051 can be used to push the device 1090 distally relative to the catheter 1057 or to hold the device 1090 steady as the catheter is retracted. In FIG. 10, the catheter 1057 is retracted proximally from the device 1090 and/or the device 1090 is advanced distally from the catheter 1050 such that owing to the offset 1055, leaf spring 1044 elastically rebounds first, while leaf spring 1090 is still constrained in a straight position by distal segment 1056 of the shaft 1057. Thus, allowing the user to selectively grab and/or restrain one leaflet in the space 1053. In FIG. 11, the user then retracts and/or pushes the device 1090 further out to the catheter 1057 such that the $2^{nd}$ ventricular leaf-springs 1042 too elastically rebounds to allow the user to now grab and or constrain the $2^{nd}$ leaflet. Once both leaflets are grabbed and or constrained, the user can then fully deploy the device 1090, wherein, the leaflets are constrained within the spaces 1047 and 1048 of the device.

FIG. 13 shows the exemplary embodiment when fully deployed (as in FIG. 8). Note that leaflets are not shown for simplicity.

Figure 14:
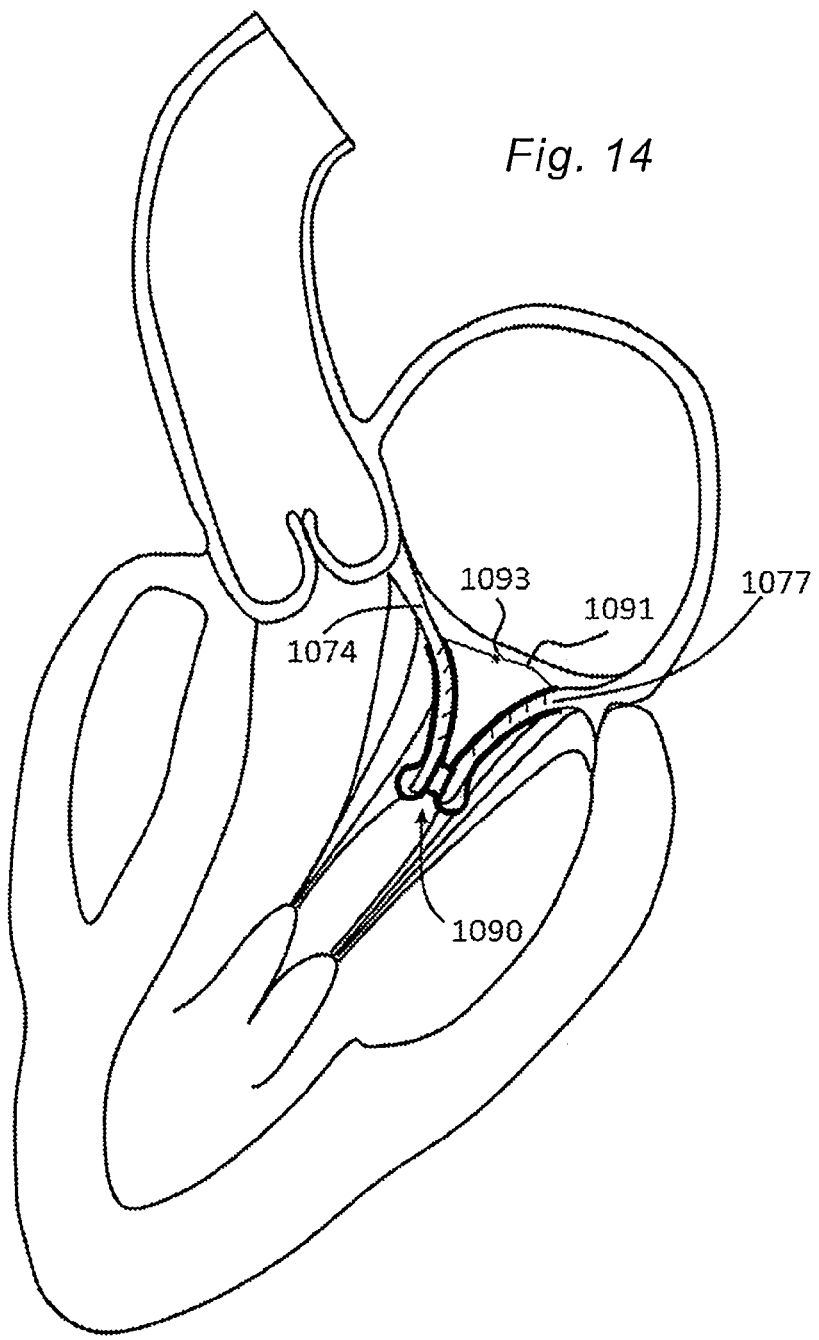
FIG. 14 shows the exemplary embodiment 1090 when deployed in mitral valve of a heart.

FIG. 14 shows an example of the device 1090 deployed within mitral valve leaflets.

Figure 20:
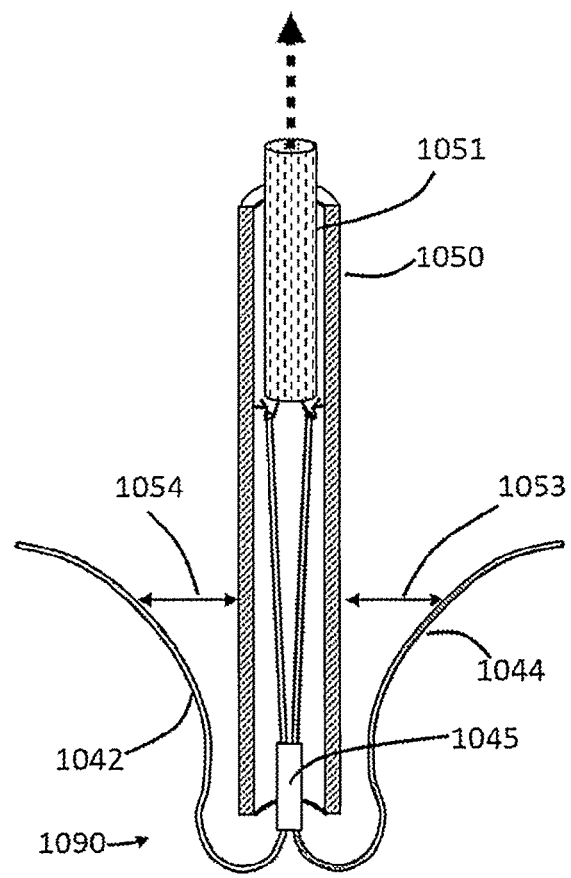
Figure 21:
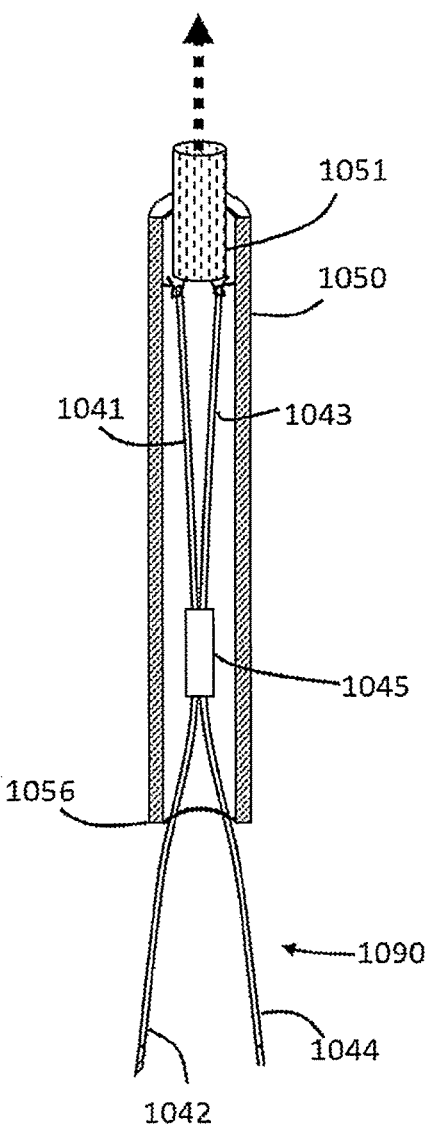
Figure 22:
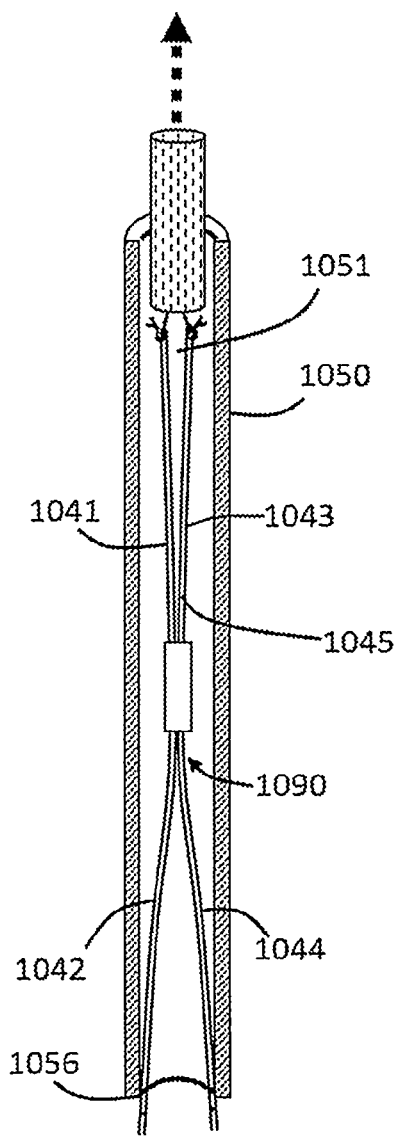

FIGS. 15-22 show a method of retrieving the exemplary device embodiment 1090 post implantation. FIG. 15 shows an exemplary rat-tooth grasper 1100 that is advanced towards the implanted exemplary device 1090. FIG. 16 shows the retrieval suture 1093 grasped by the grasper 1100. FIG. 17-18 shows the grasper 1100 being retracted inside the inner catheter 1051, thereby, raising the inner arms 1041 and 1043 together as shown in FIG. 19. FIG. 20 shows the inner arms 1041 and 1043 being retracted inside the guide catheter shaft 1050. Further retraction of the implant 1090 into the guide catheter 1050 inverts the outer arms 1042 and 1044. Raising the inner arms and/or inverting the outer arms release the leaflets from the implant 1090. FIG. 22 shows the implant fully retracted inside the guide catheter 1050, at which point the entire system along with the implant 1090 can be removed completely.

Figure 23:
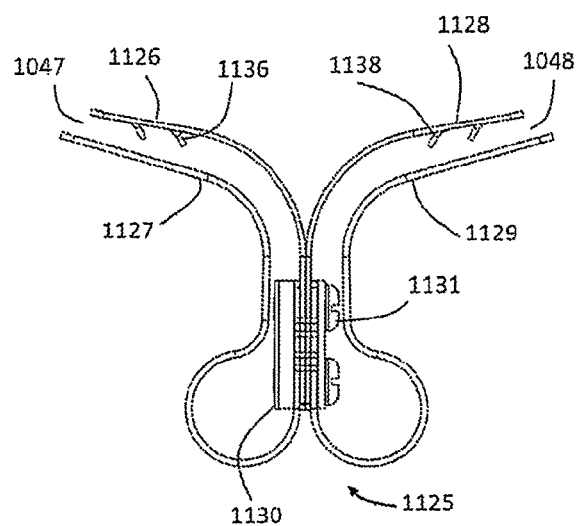
FIGS. 23-24 show an exemplary embodiment of the implant device 1130.
Figure 24:
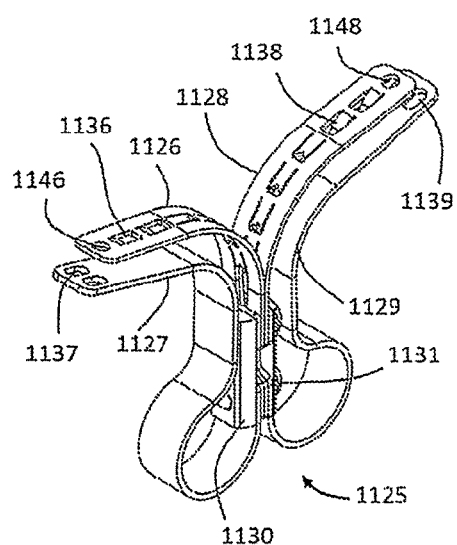

FIGS. 23 and 24 show and exemplary embodiment 1125 where the inner arms 1126, 1128 and outer arms 1127, 1129 are made of separate components. All four components are then fastened together using Base bracket 1130 and screws 1131.

Figure 25:
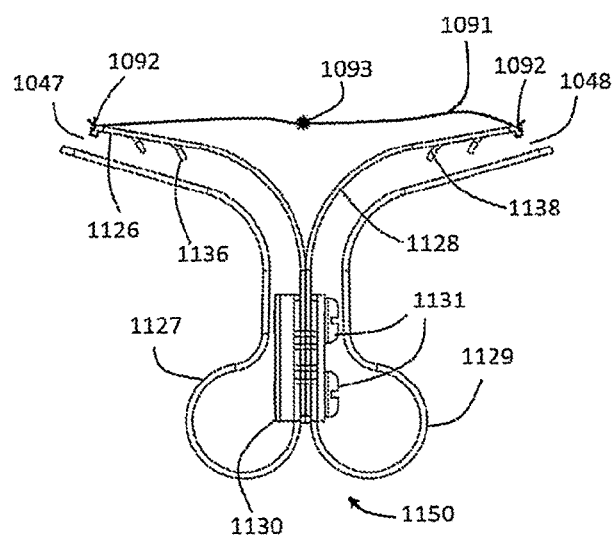
FIGS. 25-26 show an exemplary embodiment of the implant device 1150.
Figure 26:
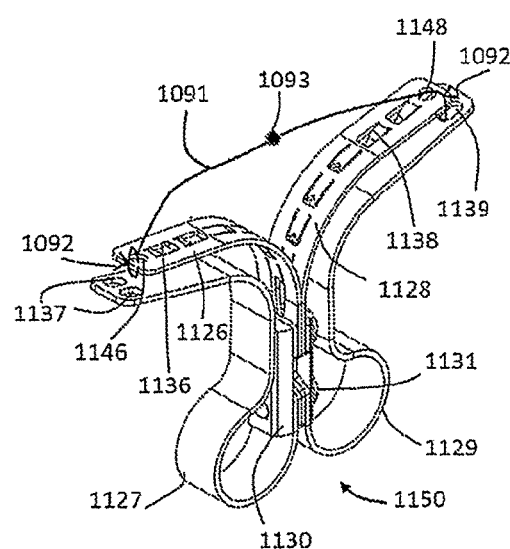

FIGS. 25 and 26 show an exemplary embodiment 1150 with retrieval suture 1091. Like embodiment 1125, it is made of individual inner arms 1126, 1128 and outer arms 1127, 1129. All four components are then fastened together using Base bracket 1130 and screws 1131.

FIGS. 27 and 28 show an exemplary embodiment 1155, wherein and expandable balloon is attached to it. During deployment procedure, the balloon is tethered to the catheter and can be inflated to reduce or mitigate the valve regurgitation.

Figure 29:
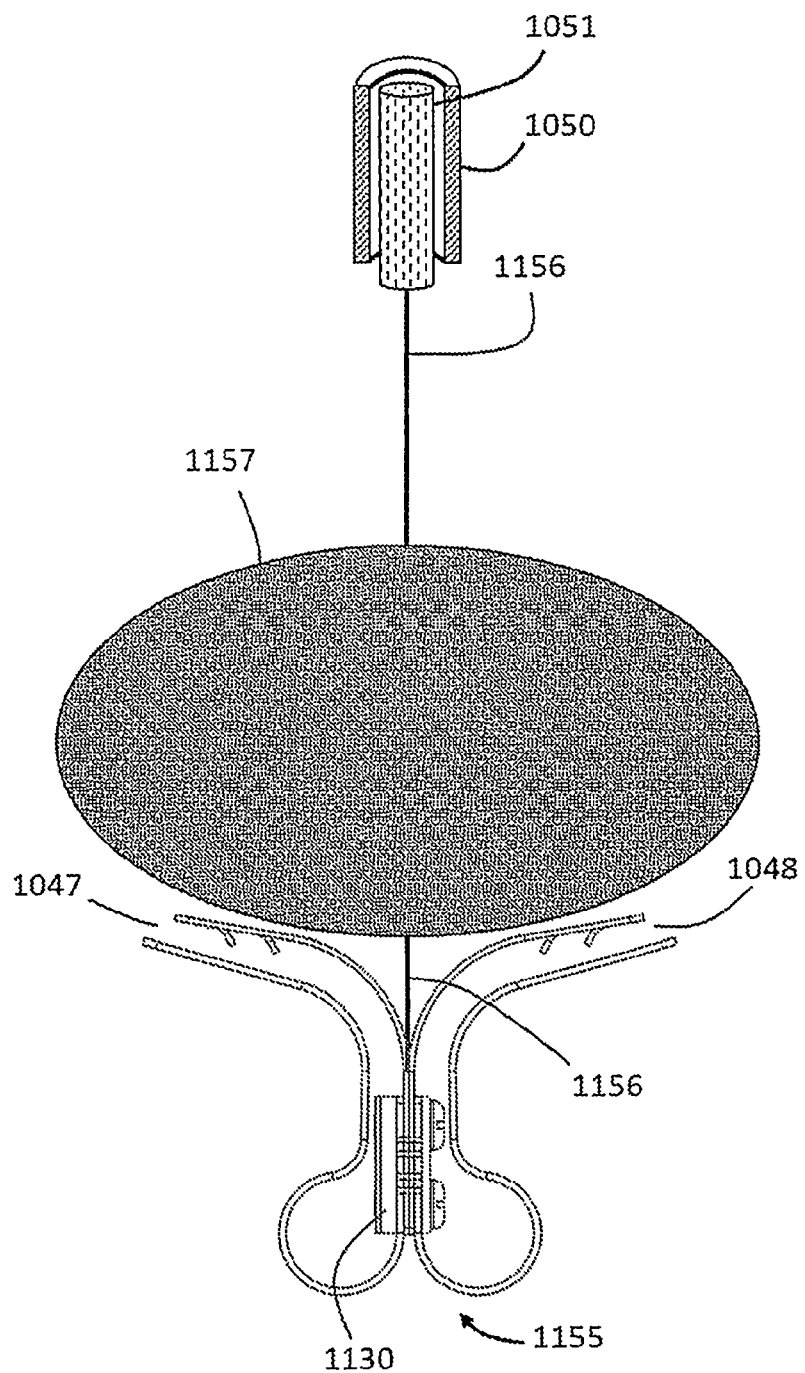

As shown in FIG. 29, the balloon can be inflated to a set pressure if it is made of low compliant material, or incrementally expanded under fluoroscopic or ultrasound guidance, until the regurgitation is mitigated if the balloon material is compliant.

Figure 30:
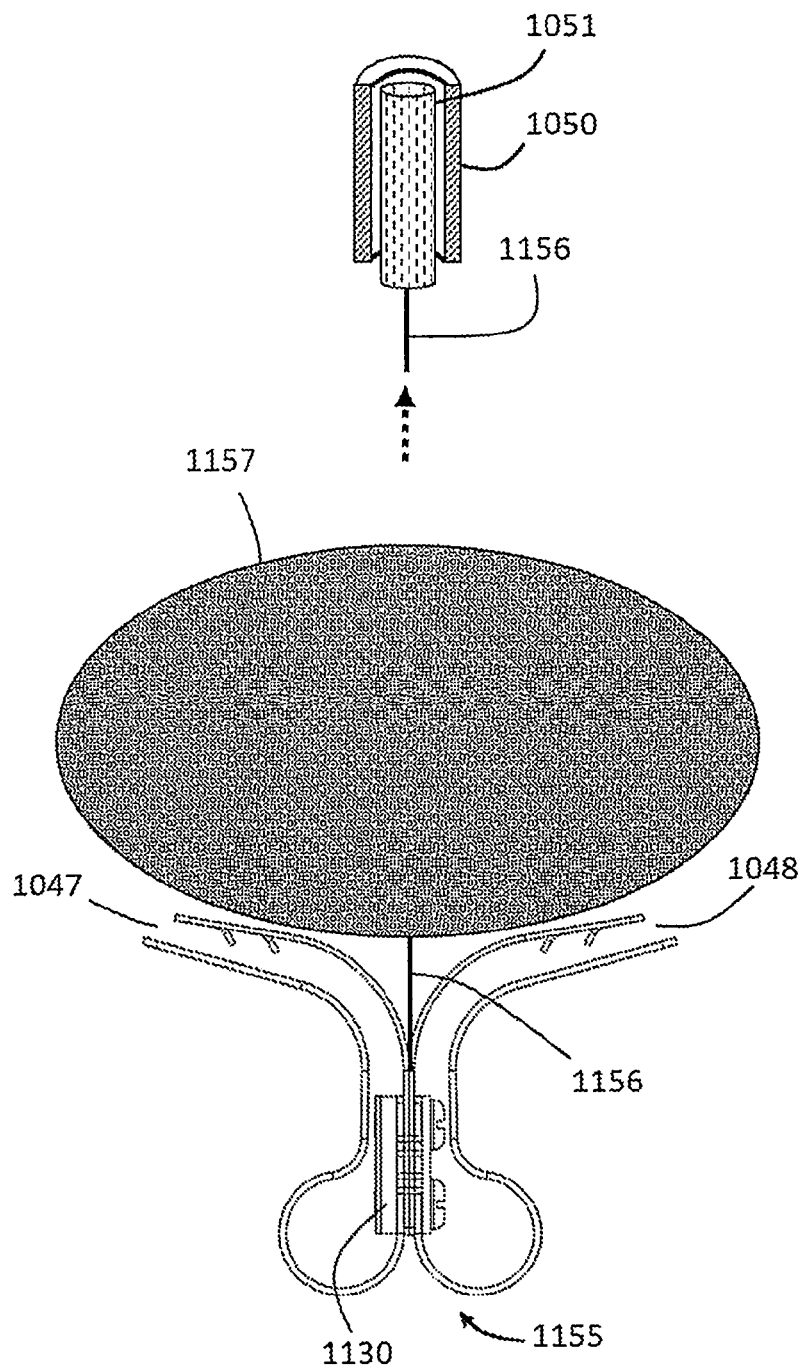

As shown in FIG. 30, the balloon with implant can be fully separated from the catheter acutely during the procedure. Any obvious and know technique of remotely inflating and implanting of the balloon may be used. For example, a technique similar to that explained in U.S. Pat. No. 9,351,862B2 may be used. Further, the balloon may have a remote tether attached to it either permanently or over a short duration, for continuous or intermittent adjustment of the balloon volume, thereby, control regurgitation.

Figure 31:
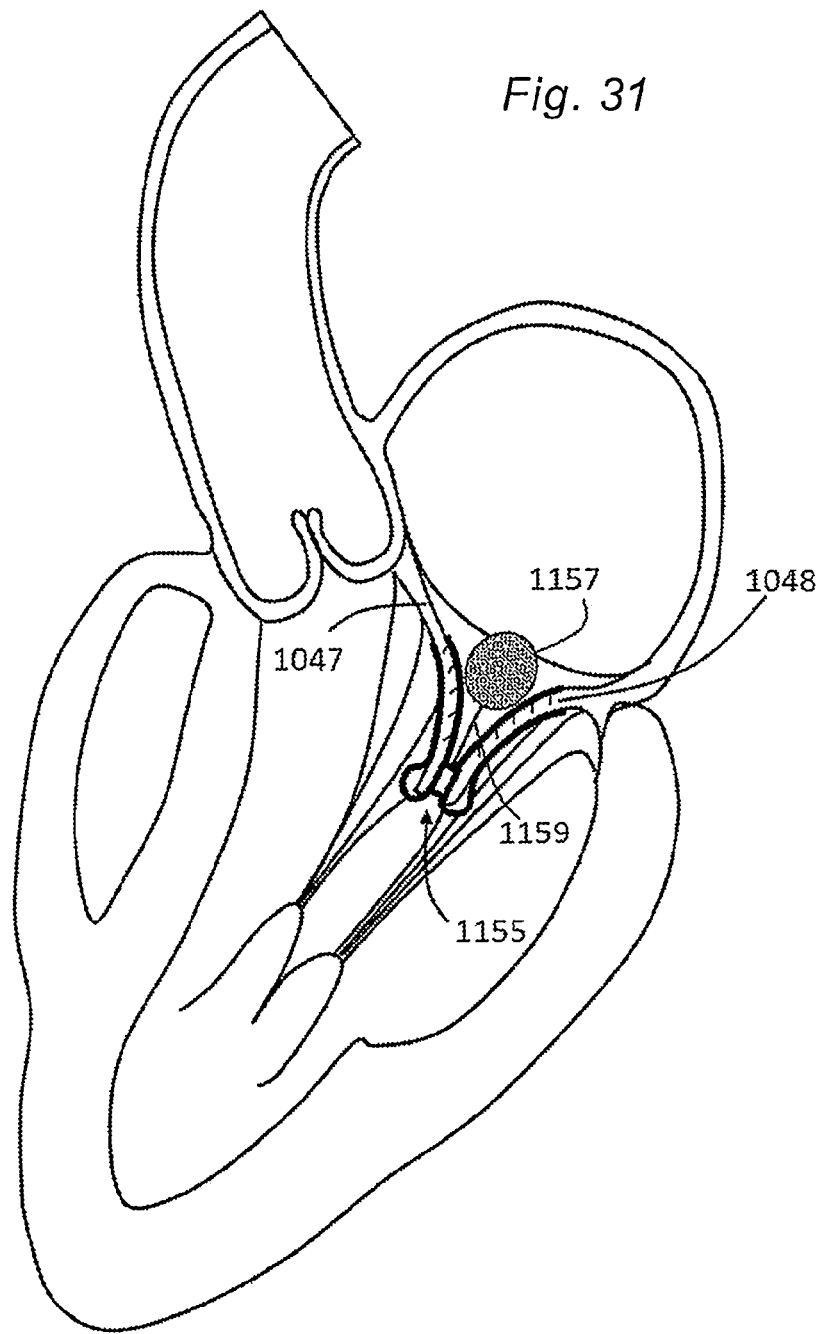
FIG. 31 shows the exemplary embodiment 1155 with expanded balloon 1157 when implanted in mitral valve of a heart.

FIG. 31 shows the schematic of implant embodiment 1155 with balloon 1157 implanted in the mitral valve.

Figure 32:
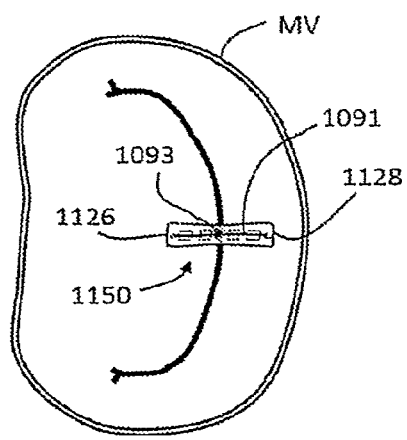
Figure 33:
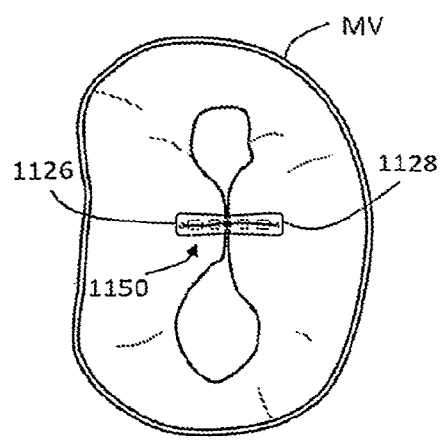
FIG. 33 shows the schematic during diastole.

FIG. 32 shows the schematic of the exemplary embodiment 1150 implanted in the mitral valve during systole, while FIG. 33 shows the schematic during diastole.

Figure 34:
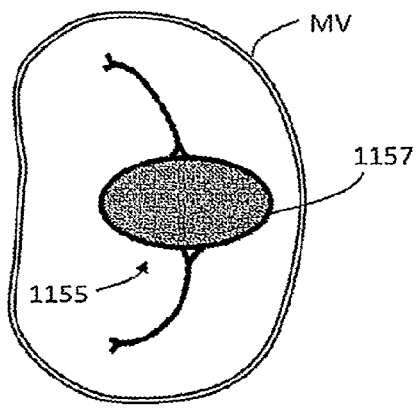
Figure 35:
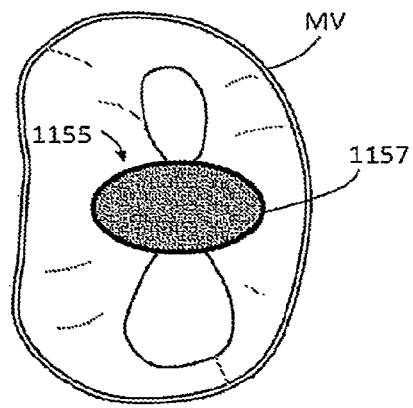
FIG. 35 shows the schematic during diastole.

FIG. 34 shows the schematic of the exemplary embodiment 1155 implanted in the mitral valve during systole, while FIG. 35 shows the schematic during diastole.

Figure 36:
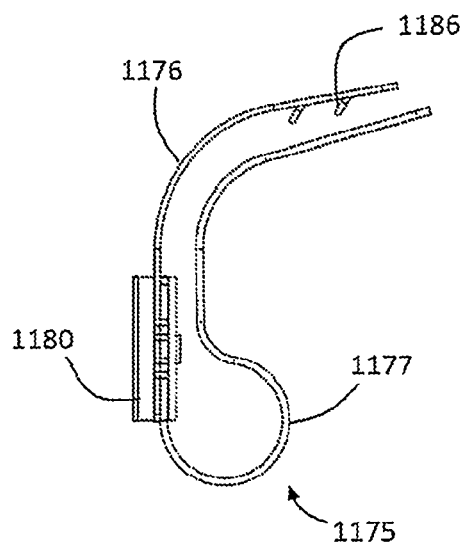
FIGS. 36-37 show an exemplary embodiment 1175 that is similar to embodiment 1030 shown in FIG. 1-2, however, the inner and outer elements are separate components that are joined together by Base Bracket 1180.
Figure 37:
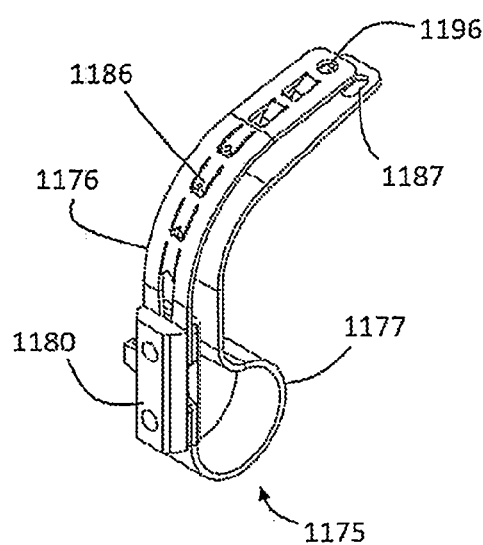

FIGS. 36-37 show an exemplary embodiment 1175 that is similar to embodiment 1030 shown in FIG. 1-2, however, the inner and outer elements are separate components that are joined together by Base Bracket 1180. An advantage of the present invention is having separate inner and outer components to allow for increased closing bias between the two components.

Figure 38:
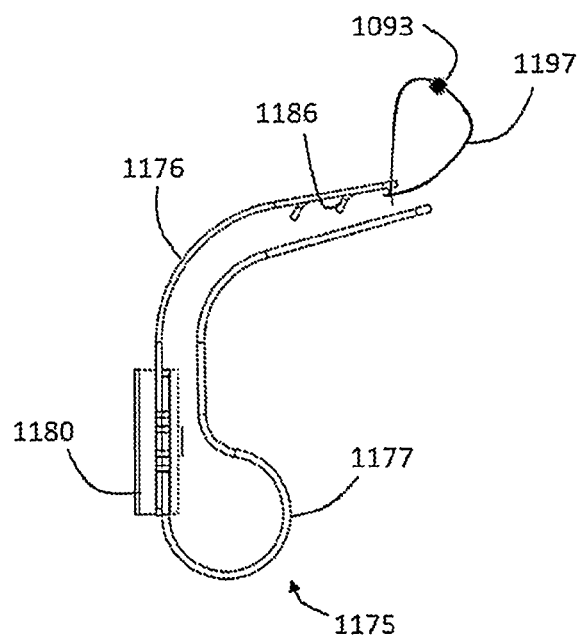
FIGS. 38-39 show a retrieval suture 1197 attached to the embodiment 1175.
Figure 39:
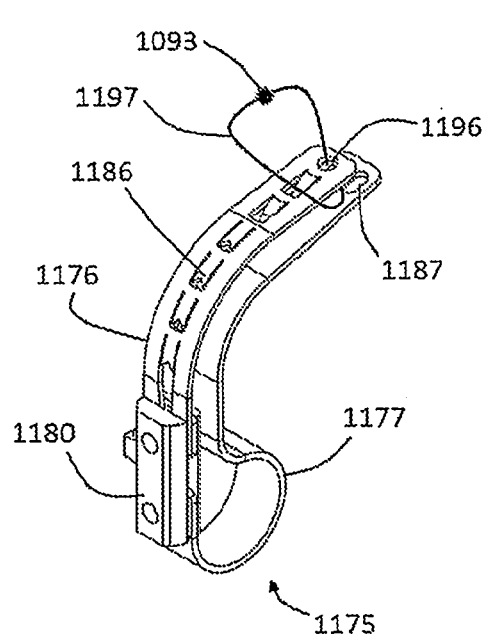

FIGS. 38-39 show a retrieval suture 1197 with a radiopaque marker 1093 attached to the embodiment 1175.

Figure 40:
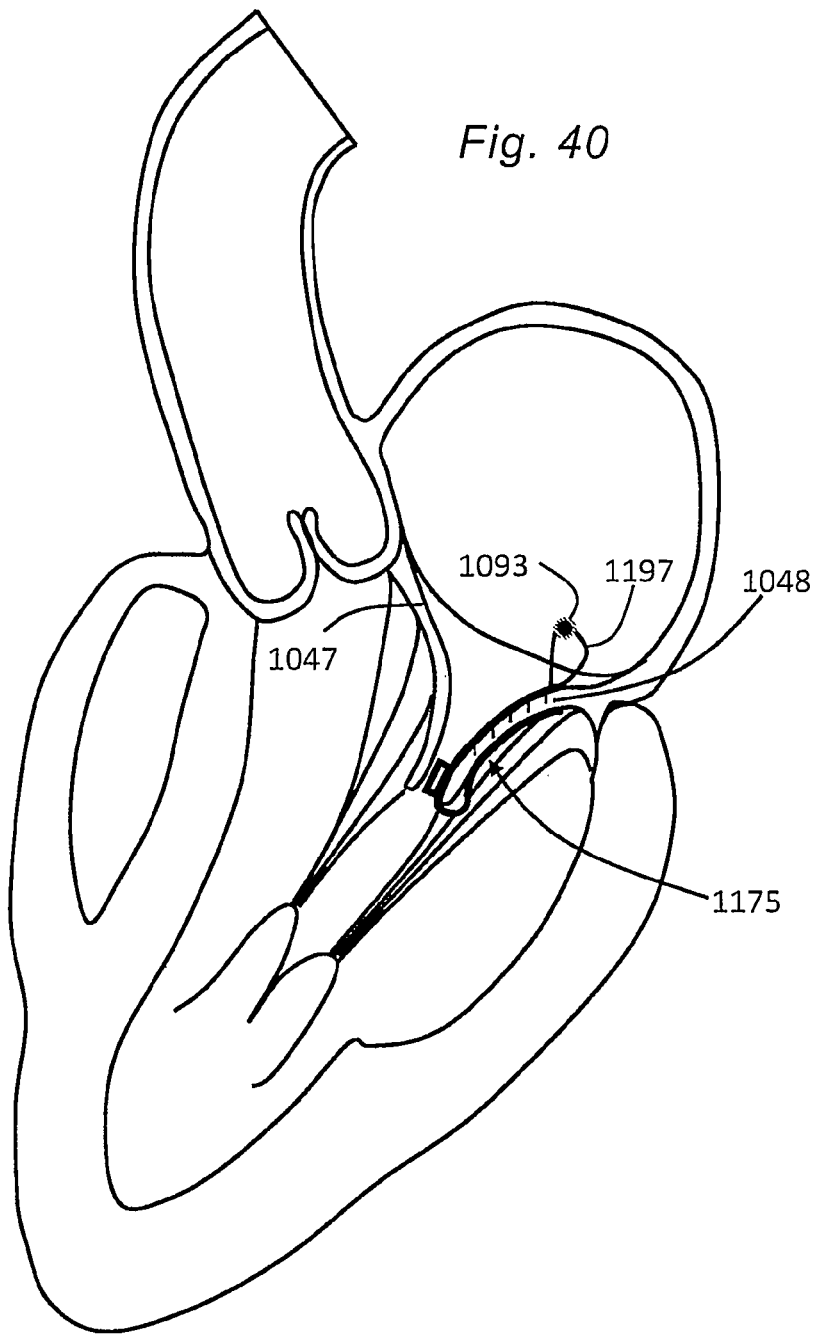
FIG. 40 shows a schematic of the embodiment 1175 implanted inside the mitral valve.

FIG. 40 shows a schematic of the embodiment 1175 implanted inside the mitral valve.

Figure 41:
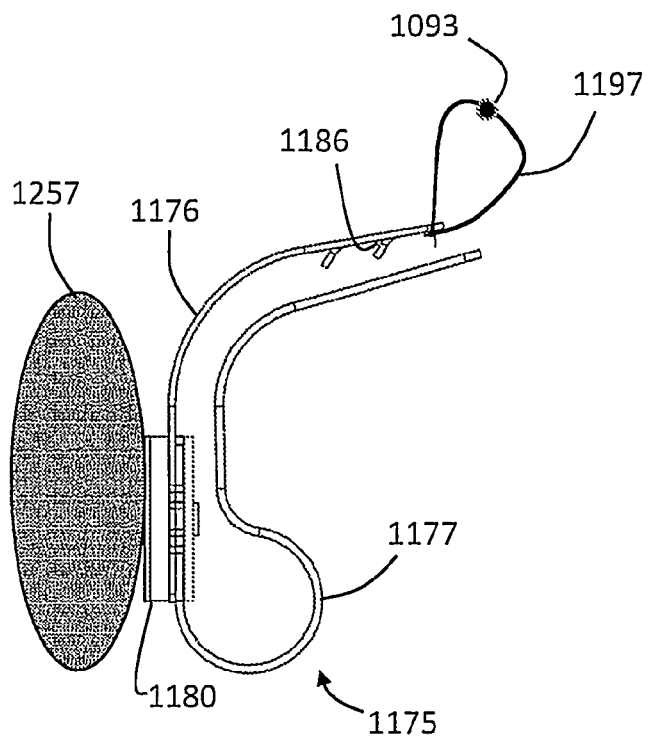
FIG. 41 shows the embodiment 1175 shown in FIG. 38, that incorporates a spacer balloon 1257.

FIG. 41 shows the embodiment 1175 shown in FIG. 38, that incorporates an exemplary spacer balloon 1257.

Figure 42:
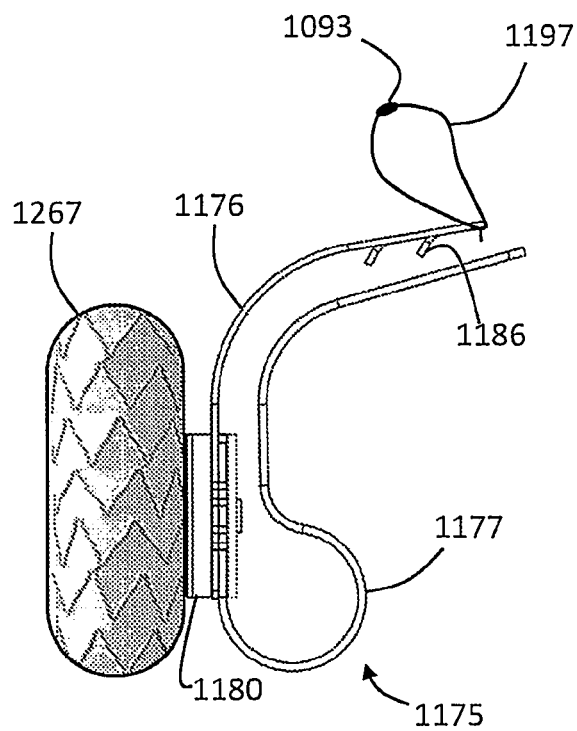
FIG. 42 shows the embodiment 1175 shown in FIG. 38, that incorporated a spacer stent like structure 1267. This structure can be self-expandable, balloon expandable or non-expandable. Further, it can be hollow, porous, covered or uncovered, coated or uncoated.

FIG. 42 shows the embodiment 1175 shown in FIG. 38, that incorporated a spacer stent like structure 1267. This structure can be self-expandable, balloon expandable or non-expandable. Further, it can be hollow, porous, covered or uncovered, coated or uncoated.

Figure 43:
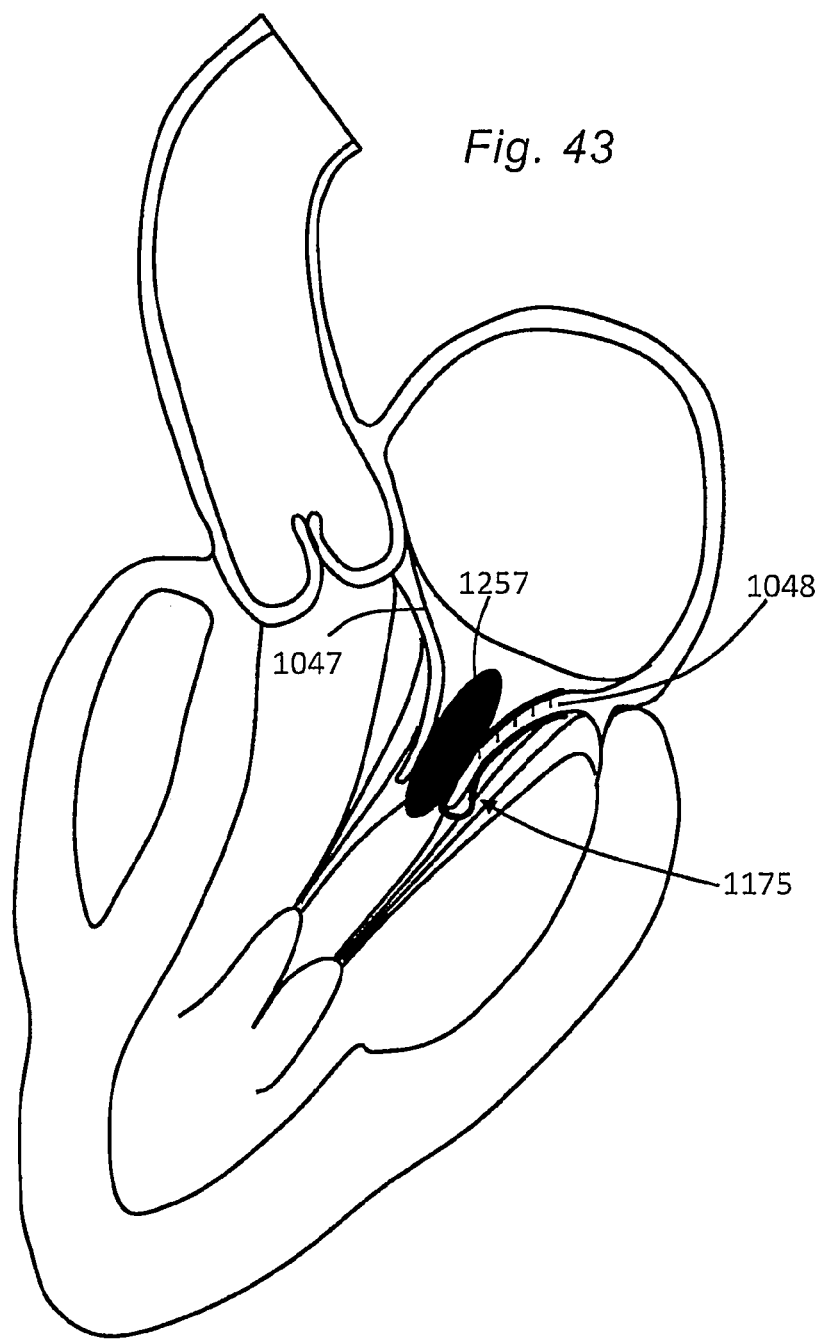
FIG. 43 shows a schematic of the embodiment 1175 previously shown in FIG. 41 implanted inside the mitral valve.

FIG. 43 shows a schematic of the embodiment 1175 previously shown in FIG. 41 implanted inside the mitral valve.

Figure 44:
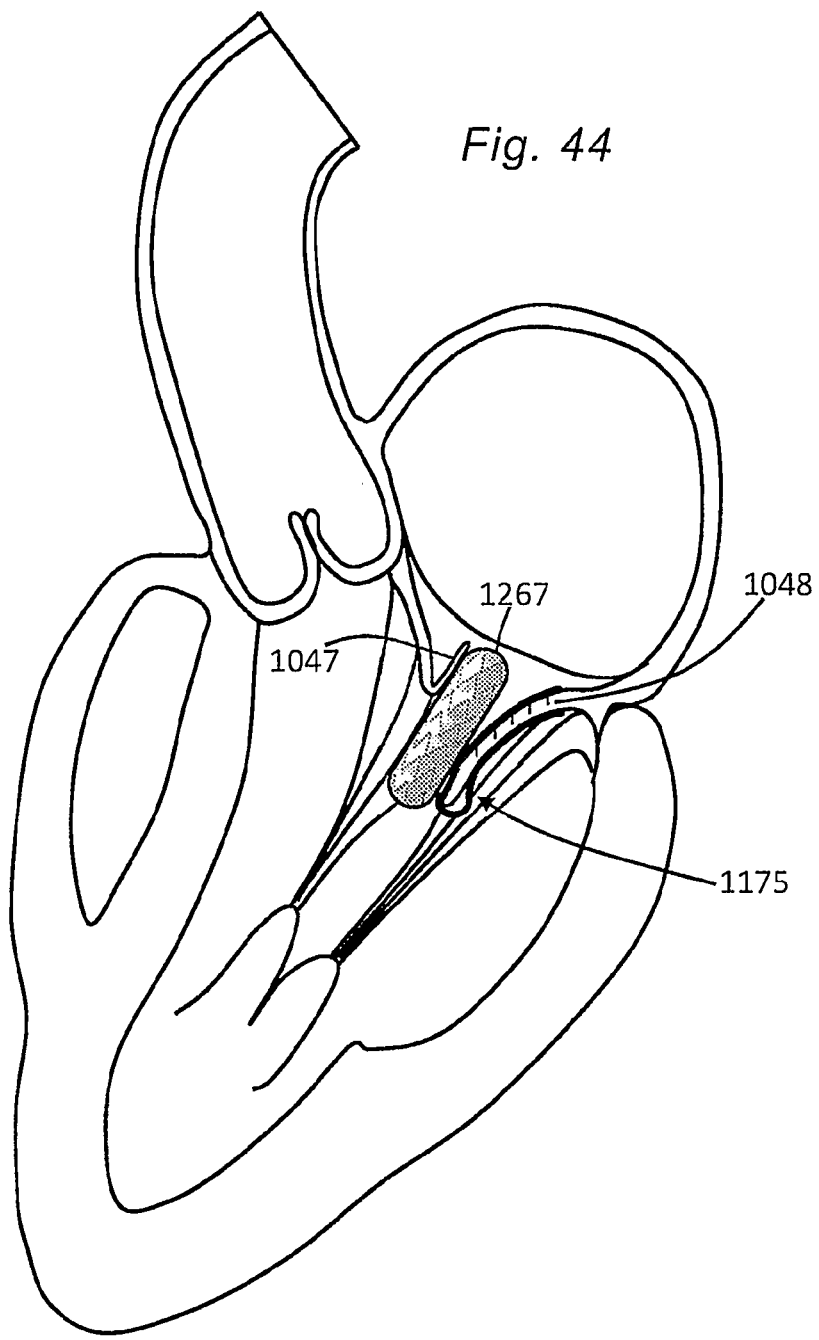
FIG. 44 shows a schematic of the embodiment 1175 previously shown in FIG. 42 implanted inside the mitral valve.

FIG. 44 shows a schematic of the embodiment 1175 previously shown in FIG. 42 implanted inside the mitral valve.

Figure 45:
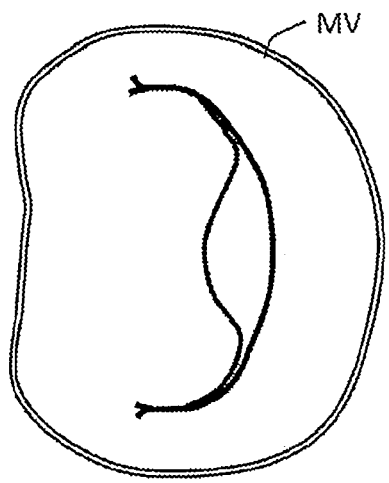
FIG. 45 shows an exemplary mitral valve during systole with regurgitant area/orifice.

FIG. 45 shows an exemplary schematic of mitral valve during systole with regurgitant area/orifice.

Figure 46:
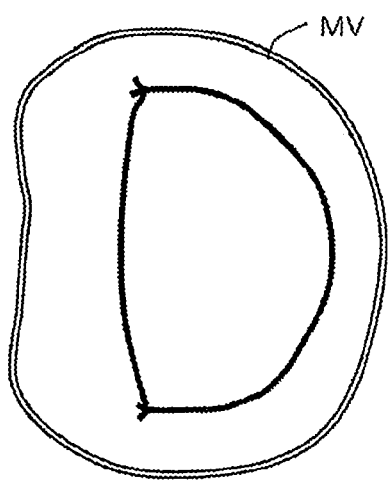
FIG. 46 shows the exemplary mitral valve of FIG. 45 during diastole.

FIG. 46 shows the exemplary schematic of mitral valve of FIG. 45 during diastole.

Figure 47:
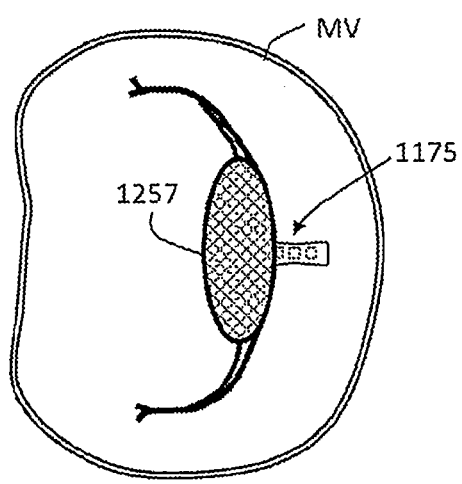
FIG. 47 shows an exemplary schematic of mitral valve during systole with balloon 1257 implanted.

FIG. 47 shows the exemplary embodiment 1175 with balloon 1257 implanted in the exemplary mitral valve during systole.

Figure 48:
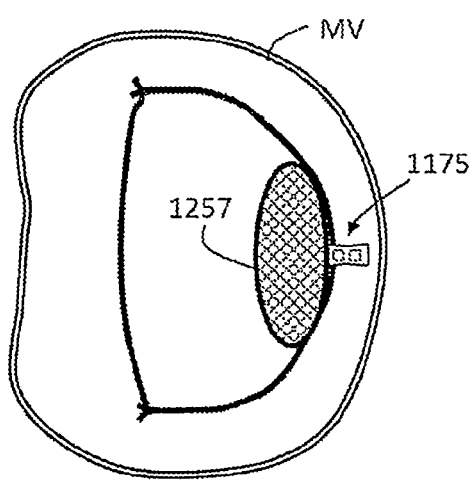
FIG. 48 shows the exemplary embodiment 1175 with balloon 1257 implanted in the same exemplary mitral valve during diastole.

FIG. 48 shows the exemplary embodiment 1175 with balloon 1257 implanted in the same exemplary mitral valve of FIG. 46 during diastole.

Figure 49:
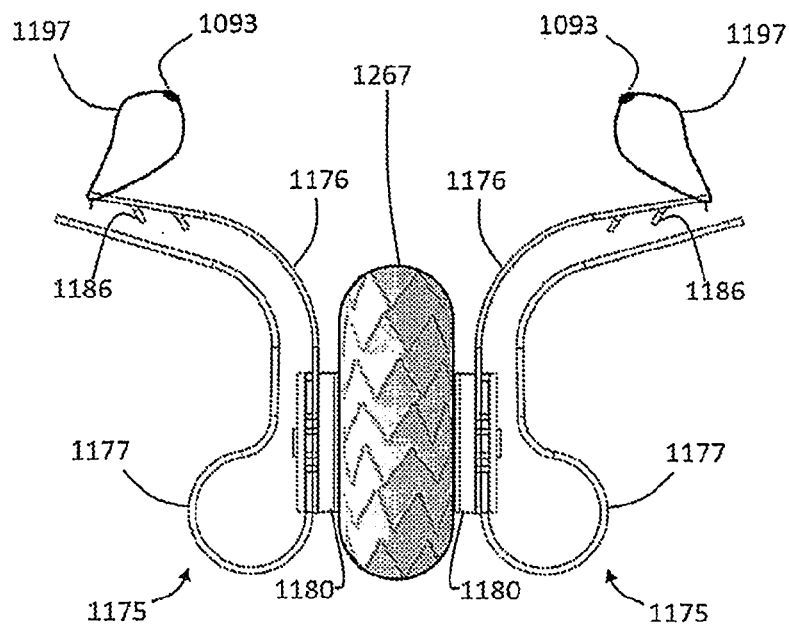
FIG. 49 shows an exemplary embodiment with two devices 1175 connected to one spacer 1257.

FIG. 49 shows an exemplary embodiment with two devices 1175 connected to one spacer 1257.

Figure 50:
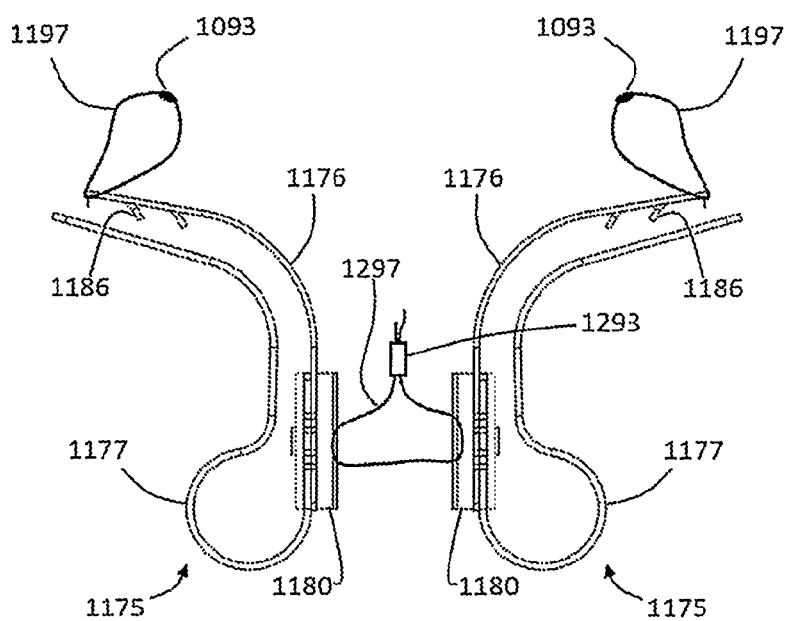
FIG. 50 shows an exemplary embodiment with two devices 1175 looped together using a suture 1257. The suture can be cinched post deployment either during the procedure or remotely post procedure.

FIG. 50 shows an exemplary embodiment with two devices 1175 looped together using a suture 1257. The suture can be cinched post deployment either during the procedure or remotely post procedure.

Unique concepts shown in this patent, for example retrieval concepts may be applicable to other designs with directly or with obvious modifications, for example, to structural heart designs as disclosed in co-owned PCT WIPO Patent Applications WO/2018/013856 and/or WO/2019/010370. Vice-versa, unique concepts taught in other co-owned patent applications may be applied to this invention, for example, sensors, transducers, actuators and/or imaging systems as described in WO/2018/013856 may be applied to this invention.

General Considerations

Commonly known interventional and minimally invasive techniques may be used to deploy any of the devices. For example, some of the approaches may be trans-septal, trans-apical, trans-atrial, and trans-aortic valve.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified elements. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

All implant embodiments described in this invention maybe optionally coated to improve biocompatibility and tissue interface.

The coatings can be metallic or polymeric. Examples of metallic coatings are: Titanium, TiN, tantalum, gold, platinum. Examples of polymeric coatings are: Fluoropolymers: PTFE, PFA, FEP, ECTFE, ETFE, Parylene, polyester, PET, polypropylene, PEEK, PVDF, HDPE, LDPE, UHMWPE, Phosphorylcholine, hydroxyapatite, THV, CaP Biodegradable: poly(lactic acid), poly(glycolic acid)

All implant embodiments maybe optionally covered to improve biocompatibility and tissue interface. The coverings can be metallic or polymeric. Additionally, the coverings can be fabric, web, fibrous, braid, woven or non-woven. Examples of metallic covering are: Titanium, tantalum, gold, platinum. Examples of polymeric coatings are: Fluoropolymers: PTFE, PFA, FEP, ECTFE, ETFE, parylene, polyester, PET, polypropylene, PEEK, PVDF, HDPE, LDPE, UHMWPE, Phosphorylcholine, hydroxyapatite, CaP, THVBiodegradable: poly(lactic acid), poly(glycolic acid).

The following is a listing of references numbers used in this application:
H Heart
MV Mitral Valve
1030 Exemplary embodiment of the implant device
1041 Inner arm, of the preferred embodiment used to capture leaflet.
1042 Outer arm, of the preferred embodiment used to capture leaflet.
1043 Inner arm, of the preferred embodiment used to capture leaflet.
1044 Outer arm, of the preferred embodiment used to capture leaflet.
1045 Base bracket, of the fixation device in the preferred embodiment.
1046 Atraumatic frictional elements of Inner Arms 1041, 1043
1047 Gap between Inner Arm 1041, 1126 and Outer Arm 1042, 1127 to capture leaflet
1048 Gap between Inner Arm 1043, 1128 and Outer Arm 1044, 1129 to capture leaflet
1049 Hole feature
1050 Catheter outer shaft (Guide catheter)
1050a Lumen of catheter outer shaft
1051 Catheter inner shaft (Delivery catheter)
1053 Gap between the Guide catheter 1050 and Outer Arm 1044
1054 Gap between the Guide catheter 1050 and Outer Arm 1042
1056 Distal edge of the outer guide catheter shaft
1057 Trailing (proximal) edge of stepped guide catheter shaft
1074 Anterior Leaflet
1077 Posterior Leaflet
1090 Exemplary embodiment of the implant device
1091 Retrieval Suture
1092 Suture loop with knot
1093 Radio Opaque marker
1100 Exemplary Rat-tooth Grasper
1101 Shaft of the Rat-tooth Grasper
1102 Claws of the Rat-tooth Grasper
1125 Exemplary alternate embodiment of the implant device 1090
1126 Inner arm, of the preferred embodiment used to capture leaflet.
1127 Outer arm, of the preferred embodiment used to capture leaflet.
1128 Inner arm, of the preferred embodiment used to capture leaflet.
1129 Outer arm, of the preferred embodiment used to capture leaflet.
1136 Atraumatic frictional elements of Inner Arm 1126
1138 Atraumatic frictional elements of Inner Arm 1128
1130 Base bracket, of the fixation device in the exemplary embodiment 1125.
1131 Exemplary fastener of the base bracket assembly
1137 Suture holes of the Outer Arm 1127
1139 Suture holes of the Outer Arm 1129
1146 Suture holes of the Inner Arm 1126
1148 Suture holes of the Inner Arm 1128
1150 Exemplary embodiment of the implant device 1125 with a retrieval suture/tether
1155 Exemplary embodiment of the implant device 1125, 1150 with a spacer balloon
1156 Proximal section of tube connecting with exemplary spacer balloon 1157
1157 Exemplary spacer balloon
1159 Distal section of tether between the spacer balloon 1157 and Base Bracket 1130
1175 Exemplary embodiment of the implant device that captures one leaflet
1176 Inner arm, of the preferred embodiment used to capture leaflet.
1177 Outer arm, of the preferred embodiment used to capture leaflet.
1176 Atraumatic frictional elements of Inner Arm 1126
1180 Base bracket, of the fixation device in the exemplary embodiment 1125.
1197 Retrieval suture
1257 Exemplary spacer: balloon
1267 Exemplary spacer: expandable covered stent
1293 Exemplary suture fastener
1297 Cinching suture loop Although many embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially. We therefore claim all that comes within the scope and spirit of these claims.

What is claimed is:

1. A method for implanting a closure device on a patient's native valve, the method comprising:
   providing a closure device comprising at least a first pair of capture springs including an atrial capture spring and an opposed ventricular capture spring, wherein the capture springs each have base ends and free ends, and wherein the base ends are coupled together and the free ends close together when unconstrained and elastically separate in response to a separating force;
   constraining the closure device in a lumen of a delivery catheter so the atrial and posterior capture spring are straightened;
   positioning a distal end of the delivery catheter adjacent to the patient's valve;
   releasing the ventricular capture spring from the lumen of the delivery catheter to engage a ventricular surface of a valve leaflet;
   releasing the atrial capture spring from the lumen of the delivery catheter to engage an atrial surface of the valve leaflet, thereby implanting the closure device to the patient's native valve, wherein the atrial and ventricular capture springs self-close over the valve leaflet to affix to said leaflet, and wherein the closure device is detached from the delivery catheter after the closure device has been implanted; and
   capturing a capturable feature on the closure device and retrieving the closure device using the capturable feature after the closure device has been implanted and detached from the delivery catheter.

2. The method of claim 1, wherein the closure device further comprises a second pair of capture springs including an atrial capture spring and an opposed ventricular capture spring, wherein the capture springs of the second pair each have base ends and free ends and wherein the base ends are coupled together and the free ends close together when unconstrained and elastically separate in response to a separating force.

3. The method of claim 2, wherein the first and second pairs of capture springs are fixed together at their respective bases prior to constraining the closure device in the lumen of a delivery catheter so the atrial and posterior capture springs of both pairs are straightened and adjacent to each other in the lumen prior to releasing.

4. The method of claim 2, wherein releasing comprises releasing the first pair of capture springs to capture a first valve leaflet, releasing the second pair of capture springs to capture a second valve leaflet, and coupling the capture springs together at their respective bases after each pair of capture springs is secured to its respective valve leaflet.

5. The method of claim 1, wherein the delivery catheter is positioned through a septum from a right atrium to a left atrium and through a mitral valve.

6. The method of claim 1, wherein the delivery catheter is positioned through a septum from a right ventricle to a left ventricle and through a mitral valve.

7. The method of claim 1, wherein the delivery catheter is positioned through an aortic valve to a left ventricle and through a mitral valve.

8. The method of claim 1, wherein the delivery catheter is positioned through an apex of the left ventricle to a left ventricle and through a mitral valve.

9. The method of claim 1, wherein the closure device consists essentially of only the first pair of capture springs and only a single valve leaflet is captured, wherein the closure device prevents regurgitant blood flow during systole and diastole.

10. The method of claim 2, wherein the first and second pairs of capture springs are released sequentially to capture the first and second valve leaflets.

11. The method of claim 2, wherein the first and second pairs of capture springs are released simultaneously to capture the first and second valve leaflets.

12. The method of claim 1, further comprising deploying a spacer to reduce or eliminate or mitigate valve regurgitation.

13. The method of claim 12, wherein the spacer is at least one of expandable, collapsible, compressible, inflatable, solid, hollow, porous, non-porous, incompressible, or adjustable during an implantation procedure, post recovery from the procedure, and/or at a later date post procedure.

14. The method of claim 1, wherein the capturable feature is coupled to the free end of one or more of the capture springs.

15. The method of claim 1, wherein the capturable feature comprises one or more of a loop, a suture loop, an echogenic marker, or a radio-opaque marker.

16. The method of claim 1, wherein the native valve is a mitral valve, a tricuspid valve, an aortic valve, a pulmonary valve, or a venous valve.

17. The method of claim 1, wherein the capturable feature can be used to actuate at least one component of the closure device during or after implantation.

18. The method of claim 1, wherein the capturable feature is captured and the closure device is retrieved post implantation after 0 days, 1 day, 1 week, 1 month, 1 year, 10 years, 20 years, 30 years, 50 years, 100 years, or 120 years.

* * * * *